United States Patent
McCormick et al.

(10) Patent No.: US 10,493,176 B2
(45) Date of Patent: Dec. 3, 2019

(54) CURTAIN SANITIZER DEVICE AND METHOD OF USING THE SAME

(71) Applicant: Standard Textile Co., Inc., Cincinnati, OH (US)

(72) Inventors: Scott McCormick, Cincinnati, OH (US); Jonathan Jurcenko, Fairfield, OH (US)

(73) Assignee: Standard Textile Co., Inc., Cincinnati, OH (US)

( * ) Notice: Subject to any disclaimer, the term of this patent is extended or adjusted under 35 U.S.C. 154(b) by 283 days.

(21) Appl. No.: 15/481,864

(22) Filed: Apr. 7, 2017

(65) Prior Publication Data
US 2018/0289847 A1  Oct. 11, 2018

(51) Int. Cl.
*A61L 2/00* (2006.01)
*G01N 21/00* (2006.01)
*A47H 23/00* (2006.01)
*A61L 2/10* (2006.01)

(52) U.S. Cl.
CPC ............ *A61L 2/10* (2013.01); *A61L 2202/11* (2013.01); *A61L 2202/122* (2013.01); *A61L 2202/14* (2013.01); *A61L 2202/16* (2013.01); *A61L 2202/24* (2013.01); *A61L 2202/26* (2013.01)

(58) Field of Classification Search
CPC . A61L 2/00; A61L 2/0047; A61L 2/10; A47H 13/00; A47H 1/19
USPC ............... 422/24, 28–29, 32, 121–122; 250/455.11, 454.11; 160/237, 330
See application file for complete search history.

(56) References Cited

U.S. PATENT DOCUMENTS

| | | | |
|---|---|---|---|
| 3,078,525 A * | 2/1963 | Grahm | A61L 2/10 250/455.11 |
| 4,907,316 A | 3/1990 | Kurz | |
| 8,662,705 B2 | 3/2014 | Roberts | |
| 9,198,990 B2 | 12/2015 | Fletcher | |
| 9,210,784 B2 * | 12/2015 | Antoniazzi | A61L 2/10 |
| 9,504,345 B2 | 11/2016 | Stibich et al. | |
| 2013/0004367 A1 * | 1/2013 | Roberts | A61L 2/10 422/24 |
| 2015/0205985 A1 | 7/2015 | Jinadatha | |
| 2015/0367008 A1 | 12/2015 | Romo et al. | |

* cited by examiner

*Primary Examiner* — Monzer R Chorbaji
(74) *Attorney, Agent, or Firm* — Wood Herron & Evans LLP

(57) ABSTRACT

A curtain sanitizer device and method, such as for use in the healthcare industry, is disclosed that can sanitize at least a portion of the surface of a hung curtain, e.g. a privacy curtain, by directing UV-C light thereat to kill or inactivate harmful microorganisms thereon that can cause infectious disease, thereby reducing the risk of spreading infectious disease. In one example, at least a portion of opposite surfaces or sides of the hung curtain can be simultaneously sanitized. The curtain sanitizer device and method can allow the curtain to be cleaned in place, and can be easier to use and less costly and time consuming than other currently available methods and devices.

43 Claims, 15 Drawing Sheets

CURTAIN SANITIZER DEVICE AND METHOD OF USING THE SAME

TECHNICAL FIELD

The present invention relates generally to a device for sanitizing surfaces to reduce the risk of spreading infectious disease and, more specifically, to a curtain sanitizer device, such as for use in the healthcare industry, that can sanitize the surface of a hung curtain, e.g., a privacy curtain, by directing germicidal ultraviolet light thereat to kill or inactivate harmful microorganisms thereon, thereby reducing the risk of spreading infectious disease.

BACKGROUND

In recent years, healthcare-acquired infections (HAI's) have become a growing concern. Notably, many patients admitted to a hospital already have a weakened immune system making it very easy for them to get infected by a contaminated surface. In particular, the Centers for Disease Control and Prevention (CDC) estimates that 1 out of every 25 patients who are admitted to a hospital will contract a HAI and, of those, 1 out of every 9 patients will succumb to the infection. Every year this results in more than two million patients contracting HAI's causing an estimated 100,000 deaths.

One of the leading causes of HAI's occurs when hospital staff, for example, do not maintain proper sanitizing procedures, such as washing their hands in-between seeing patients. This can lead to the spread of harmful microorganisms onto many surfaces in a patient's room, with one of the most frequent surfaces being that of the privacy curtain, which may be repeatedly touched, e.g., opened and closed, by unwashed staff hands. The privacy curtain also can become unsanitary from touching by patients and/or other visitors or through any number of other ways, including accidental contact with infected blood, urine, and/or feces, for example.

Various methods and devices have been employed over the years in an effort to reduce the spread of infectious disease via unsanitary curtains. In one example, the curtain is simply removed and laundered. However, each curtain is often a unique length and designed such that each one must be tracked so as to go back to the same location. Then, each curtain must be reinstalled in the room. This can be a very time consuming and expensive process, often taking several hours of labor for a single hospital employee. Further complicating the issue, as a result of the difficulty and time required to keep privacy curtains sanitary, such curtains too often are either not cleaned properly or just not enough.

While it is recognized that laundering unsanitary curtains may be the best or only option in certain circumstances, regular laundering to remove harmful microorganisms that can cause infectious disease may not be necessary to maintain sanitary conditions. To that end, non-laundering methods and associated devices have also been applied to curtains in an effort to simplify the sanitizing process. In one example, a chemical disinfectant is used to wipe down the curtain, in place. However, this method can be difficult to perform because curtains, e.g., privacy curtains, are not nearly as easy to clean as a solid surface, such as countertop. Another method involves switching from reusable to disposable curtains. However, many hospitals do not have sufficient storage capacity for a surplus inventory of disposable curtains, and replacing the curtain in every room can be a time consuming and expensive process. And given the frequency of how often disposable curtains should be changed on a daily basis, both of these reasons tend to lead to disposable curtains not being replaced as often as needed.

Another method for sanitizing curtains includes using an ultraviolet area sterilizer (UVAS) to sterilize an entire room. With this method, the time required to sanitize an object within the room, e.g., a privacy curtain, is calculated by factoring in the distance from the ultraviolet (UV) light source to the object. Given how far away each object in an average patient/surgical room is, complete room sterilization can take as long as several hours. Furthermore, there is the chance that some areas of the room, specifically the privacy curtain if it is bunched up, may not be completely sanitized. Finally, these UVAS machines can be very expensive costing as much as $100,000 per unit.

In still yet another example, germicidal UV hand-held wands have been used to sterilize the surfaces of various objects. These wands can operate using incandescent or fluorescent ultraviolet-C (UV-C) lights. However, there are many limitations to the use of currently available UV light wands. For example, such devices can give non-uniform exposure because the user merely waves the light over the surface. Also each user is different and, thus, yields a different level of efficacy. Further, there is a concern with respect to UV-C exposure to users and bystanders because UV-C radiation can be more damaging to human eyes and more carcinogenic to skin than UV-A and UV-B radiation.

It thus would be beneficial to provide a device and method for sanitizing hung curtains, such as in a healthcare setting, that can reduce the risk of spreading infectious diseases and that can be safe and easy to use and can be less costly and time consuming than other currently available methods and devices.

SUMMARY

UV light is known as a highly effective means of destroying microorganisms. At an optimal wavelength of 254 nm, shortwave UV-C light exposure can kill or inactivate bacteria, molds, protozoa, yeasts, and viruses on the surfaces of objects, including eliminating in certain circumstances over 99% and greater of surface microbes, including those that can cause and lead to the spread of infectious diseases.

The present invention utilizes UV-C radiation or light to reduce the risk of spreading infectious diseases through direct contact with curtains, such as those used in healthcare settings. More specifically, the present invention is directed to a curtain sanitizer device and method, such as for use in the healthcare industry, that can sanitize at least a portion of the surface of a hung curtain, e.g., a privacy curtain, by directing UV-C light thereat to kill or inactivate harmful microorganisms thereon that can cause infectious disease, thereby reducing the risk of spreading infectious disease.

In one embodiment, the curtain sanitizer device includes a base, and spaced apart and opposing first and second elongated walls extending in a vertical direction away from the base. The first wall includes an inner surface that is in opposing relationship to an inner surface of the second wall, with at least one of the inner surfaces configured to accommodate at least one UV-C light, which is capable of killing or inactivating harmful microorganisms on a hung curtain. The space between the inner surface of the walls defines a curtain channel having opposing side openings and an open distal end to allow at least a portion of the hung curtain to pass through the curtain channel and be sanitized by the at least one UV-C light. In one example, at least one inner surface includes at least one recessed channel extending along a length of the wall to accommodate at least one UV-C light. In another example, the device can simultaneously sanitize opposite side surfaces of a hung curtain.

In another embodiment, the curtain sanitizer device includes spaced apart and opposing first and second elongated walls extending in a vertical direction and in parallel relation to one another. The first wall includes an inner surface that is in opposing relationship to an inner surface of the second wall, with each inner surface configured to accommodate at least one UV-C light, which is capable of killing or inactivating harmful microorganisms on a hung curtain. A back wall connects the first and second elongated walls together. The back wall includes an outer surface that is configured to be permanently or removably mounted to a wall such that the device defines a wall mounted unit. The space between the inner surface of the first, second, and back wall defines a curtain channel having only one side opening opposite the back wall and an open distal end to allow at least a portion of the hung curtain to pass through the curtain channel and be sanitized by the at least one UV-C light. In one example, at least one inner surface of the first and second walls includes at least one recessed channel extending along a length of the wall to accommodate at least one UV-C light. In another example, the device can simultaneously sanitize opposite side surfaces of a hung curtain.

In another embodiment, a method for sanitizing a hung curtain includes passing a hung curtain through a curtain channel of a curtain sanitizer device. The curtain channel includes a treatment zone having at least one UV-C light capable of emitting radiation onto at least a portion of one side of the hung curtain. Then subjecting the portion of the one side of the hung curtain to emitted radiation from the UV-C light as the hung curtains passes through the treatment zone, thereby killing or inactivating harmful microorganisms on the portion of the one side of the hung curtain to sanitize the hung curtain. In one example, the device can simultaneously sanitize opposite side surfaces of a hung curtain.

The curtain sanitizer device and method can allow the hung curtain to be sanitized in place, which can be easier to use and less costly and time consuming than other currently available methods and devices.

BRIEF DESCRIPTION OF THE DRAWINGS

The accompanying drawings, which are incorporated in and constitute a part of this specification, illustrate embodiments of the invention and, with a detailed description of the embodiments given below, serve to explain the principles of the invention.

DETAILED DESCRIPTION OF SPECIFIC EMBODIMENTS

FIGS. 1-14 show various embodiments of a curtain sanitizer device 10, 10A, 10B, 100, 100A, and 200, in accordance with the present invention. As explained in more detail further below, the curtain sanitizer device 10, 10A, 10B, 100, 100A, 200 can sanitize at least a portion of a side surface 12a and 12b of a hung curtain 14, e.g., a privacy curtain, such as those used in healthcare settings, by directing germicidal ultraviolet light thereat to kill or inactivate harmful microorganisms thereon that can cause infectious disease, thereby reducing the risk of spreading infectious disease. Specifically, UV-C light can be utilized to kill or inactivate bacteria, molds, protozoa, yeasts, and viruses on the surfaces of curtains, such as privacy curtains used in hospitals, eliminating in certain circumstances over 99% and greater of surface microbes, including those that can cause and lead to the spread of infectious diseases. In one example, the UV-C light can emit radiation having a wavelength of 100 nm-280 nm. In another example, the UV-C light can emit radiation having a wavelength of approximately 254 nm. In one example, the device 10, 10A, 10B, 100, 100A, 200 can simultaneously sanitize at least portions of opposite side surfaces 12a, 12b of the curtain 14. The curtain sanitizer device 10, 10A, 10B, 100, 100A, 200 can allow the curtain 14 to be cleaned in place and can be safer and easier to use and less costly and time consuming than other currently available methods and devices.

Use of the descriptive terms such as top, bottom, front, back, vertical, and/or horizontal hereinbelow, for example, as it pertains to/describes the device 10, 10A, 10B, 100, 100A, 200 is from the viewpoint of a user of the device 10, 10A, 10B, 100, 100A, 200 (when properly used), unless otherwise noted.

Figure 1:
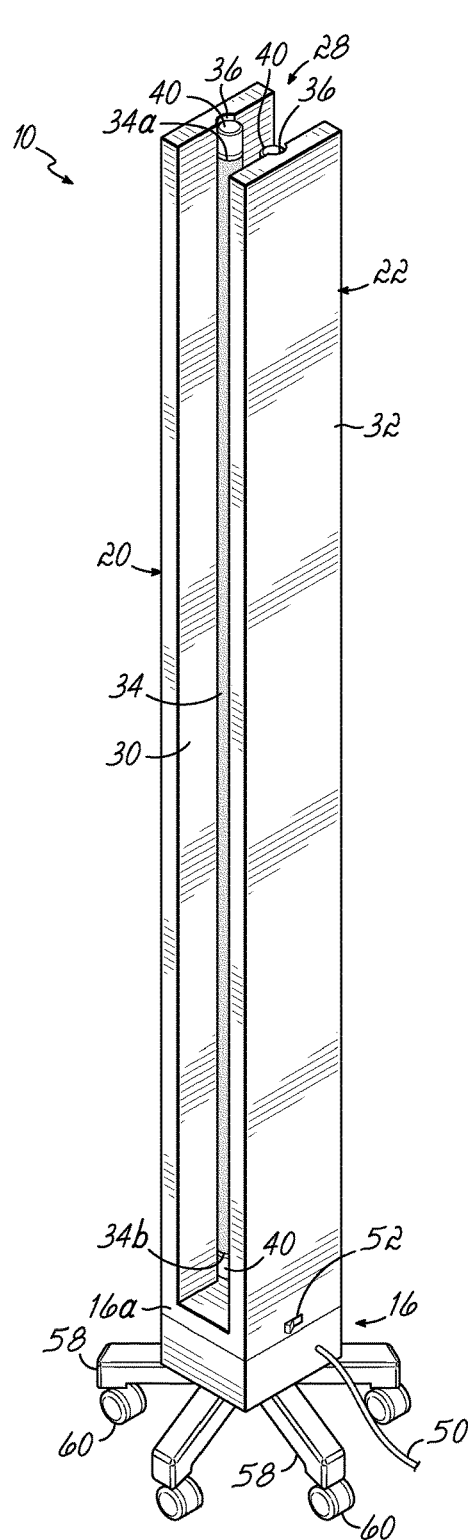
FIG. 1 is a perspective side view of a curtain sanitizer device in accordance with an embodiment of the present invention.
Figure 2:
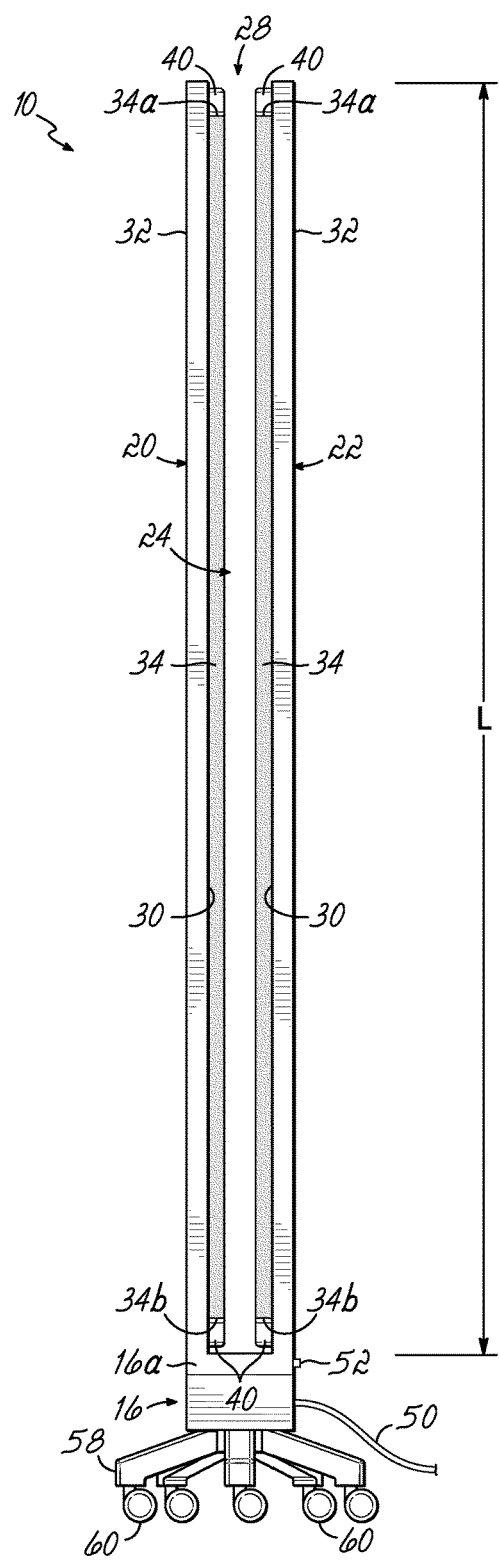
FIG. 2 is a side elevational view of the curtain sanitizer device of FIG. 1.
Figure 3:
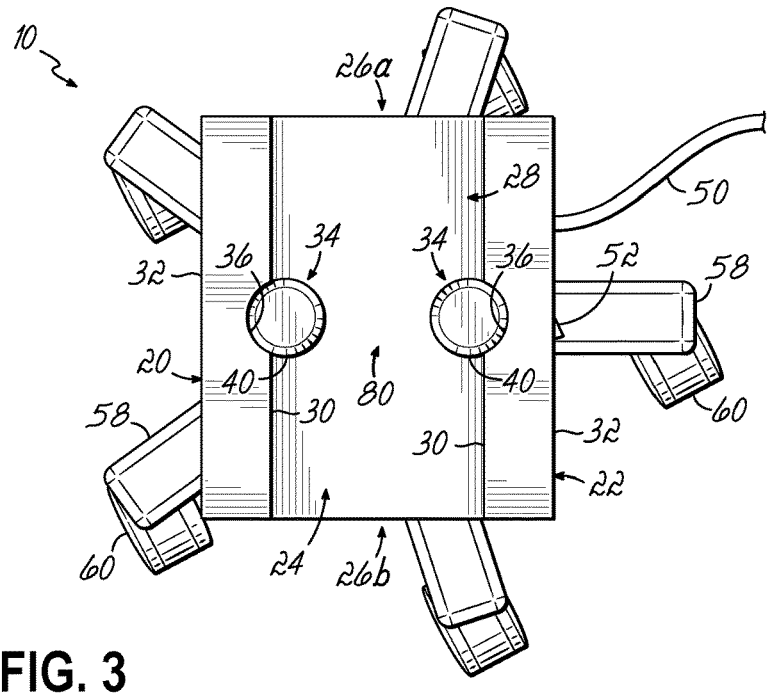
FIG. 3 is a top view of the curtain sanitizer device of FIG. 1.

With reference now to FIGS. 1, 2, and 3 and in accordance with an embodiment of the present invention, curtain sanitizer device 10 is shown including a base 16 and spaced apart and opposing first and second elongated walls 20 and 22 extending in a direction generally perpendicularly away from the base 16. In one example, the walls 20, 22 extend in a vertical direction away from the base 16. The walls 20, 22 and base 16 cooperate to define a generally U-shaped configuration with the spacing between the walls 20, 22 defining a curtain channel 24 that has elongated first and second side openings 26a and 26b and an open top or distal end 28, which allow a hung curtain 14 (See, e.g., FIG. 4), such as a privacy curtain, to pass or be moved therethrough for sanitizing at least a portion of the side surfaces 12a, 12b thereof, as further described below.

The walls 20, 22 can include relatively flat and opposing inner surfaces 30 and relatively flat outer surfaces 32. Each wall 20, 22 can be configured to accommodate one or more UV-C lights 34, with each light 34 being associated with each inner surface 30 of the walls 20, 22. In one example, the inner surface 30 can include an optional recessed channel 36 extending approximately centrally along about the length (L) of the wall 20, 22 for receiving the UV-C light 34. The recessed channel 36 generally can be sized, shaped, and/or configured to accommodate a complimentary size, shape, and/or configuration of the UV-C light 34. In this example, each UV-C light 34 defines an elongated tube with the recessed channel 36 being concave, or defining a generally semicircular shape, to accommodate the UV-C light 34. Opposing ends 34a and 34b of each UV-C light 34 can cooperate with a corresponding electrical contact 40, e.g., a light socket, which may be situated in the recessed channel 36, at approximately opposing ends of the wall 20, 22 for receiving the UV-C light 34 to provide an electrical connection from the device 10 to allow the UV-C lights 34 to be turned on and off, as discussed further below. Because there is a concern with respect to UV-C exposure to users and bystanders insofar as UV-C radiation can be more damaging to human eyes and more carcinogenic to skin than UV-A and UV-B radiation, the width (W) of each wall 20, 22 is such that the wall 20, 22 extends, in both directions, beyond its associated UV-C light(s) 34, which permits the device 10, along with the presence of the optional recessed channel 36, to reduce or eliminate any potential UV-C radiation exposure to users and bystanders.

As discussed above, the recessed channel 36 can take on any number of various sizes (e.g., shorter, narrower, wider, etc.), shapes (e.g., squares, rectangles, circles, etc.), and/or configurations (e.g., s-shaped, etc.) to accommodate a corresponding UV-C light(s) 34. It should also be understood that more than one elongated light 34 and/or recessed channel 36 can be associated with one or both walls 20, 22. Additionally, a plurality of differently sized, shaped, and/or configured lights can be located along the inner surface 30 of one or both walls 20, 22, with or without the optional recessed channel 36. In another example, only one of the inner surfaces 30 may include a UV-C light(s) 34. Accordingly, it should be appreciated that variations of the size, shape, configuration, and/or number of the lights 34 and any corresponding recessed channel 36, if so desired, can be contemplated here. In addition, the UV-C light 34, or a plurality of lights, may extend approximately the length (L) of the wall 20, 22 or less than the length (L) of the wall 20, 22. And the manufactured length (L) of the wall(s) 20, 22 and, thus, the overall height of the device 10 may be adjusted accordingly to correspond to the height needed to desirably sanitize the target curtain(s) 14. In another example, one wall 20, 22 may be shorter or longer than the other wall 20, 22.

The UV-C light 34 may be any suitable or traditional UV-C light source, including incandescent or fluorescent UV-C lights or lamps. In one example, the UV-C light 34 can include mercury-based or non-mercury-based UV-C lamps or light bulbs. In another example, the UV-C light 34 includes one or more UV-C light emitting diodes (LEDs). In another example, the UV-C lights 34 can include at least two different types of UV-C light sources. The UV-C light 34 also may be shatter resistant. The UV-C lights 34 can have the same or different intensities, e.g. watts. In one example, the watts can range from about 1 to about 100 watts. In another example, the watts can range from about 10 to about 75 watts. A specific example of a UV-C light suitable for use here is the STER-L-RAY® Instant Start germicidal lamp, which is available from Atlantic Ultraviolet Corporate of Hauppauge, N.Y. In one example, the UV-C light 34 may be provided separately from the device, such as an after market purchase.

In one embodiment, the UV-C light 34 can emit continuous radiation. In another embodiment, the UV-C light 34 can produce different patterns of radiation. The patterns may be, for instance, pulsed, fractional, collimated, or scattered to ensure sufficient propagation of the UV-C light. In one example, the patterns may be selected and/or controlled by or via a computer processor. In one example, the inner surface 30 of the device 10 can be formed with a material that is highly reflective of UV-C radiation.

Figure 1A:
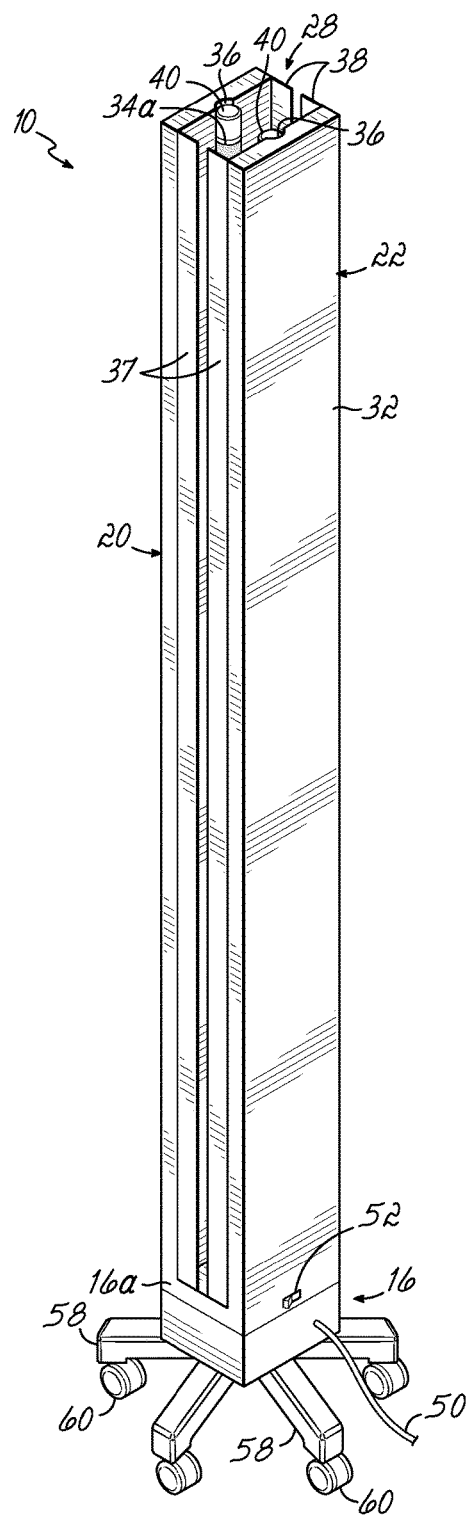
FIG. 1A is a perspective side view of the curtain sanitizer device of FIG. 1 showing the first and second walls with UV-C radiation safety guards.
Figure 3A:
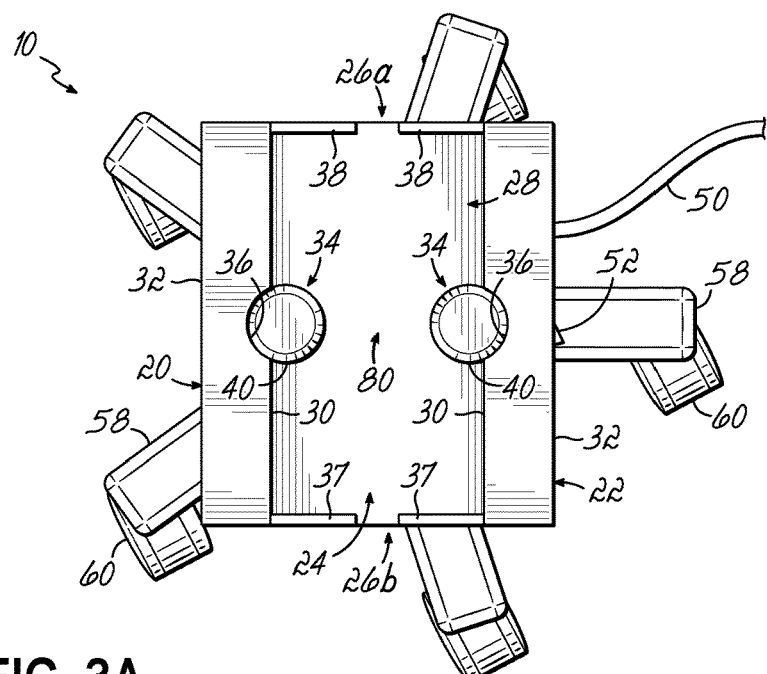
FIG. 3A is top view of the curtain sanitizer device of FIG. 1A.

In another embodiment, as shown in FIGS. 1A and 3A, each of the walls 20, 22 of the device 10A can include first and second spaced apart arms 37 and 38 that extend generally horizontally along the length of the walls 20, 22 and in a direction away from the inner surface 30 and towards the opposing wall 20, 22 so that the first and second arms 37, 38 of the first wall 20 are in spaced apart relation to the first and second arms 37, 38, respectively, of the second wall 22. In one example, the first and second arms 37, 38 may be perpendicular to the inner surface 30 of each corresponding wall 20, 22 and are spaced apart so that any corresponding recessed channel 36 and the UV-C light(s) 34 may be situated generally intermediate the first and second arms 37, 38 so as reduce or eliminate any potential UV-C radiation exposure to users and bystanders when the device 10 is in use, thereby acting as UV-C radiation safety guards. Although shown extending generally the length of the walls 20, 22, it should be understood that the arms 37, 38 may be shorter in length and can correspond in length with that of the UV-C lights 34. The spacing between the walls 20, 22 and opposing first arms 37 and opposing second arms 38 defines the curtain channel 24 that has elongated first and second side openings 26a, 26b and open top or distal end 28, which allow hung curtain 14 (See, e.g., FIG. 4), such as a privacy curtain, to pass or be moved therethrough for sanitizing at least a portion of the side surfaces 12a, 12b thereof, as further described below.

In one example, the first and second arms 37, 38 of one wall 20, 22 of the device 10B may be offset in any direction from the first and second arms 37, 38 of the second wall 22.

Figure 1B:
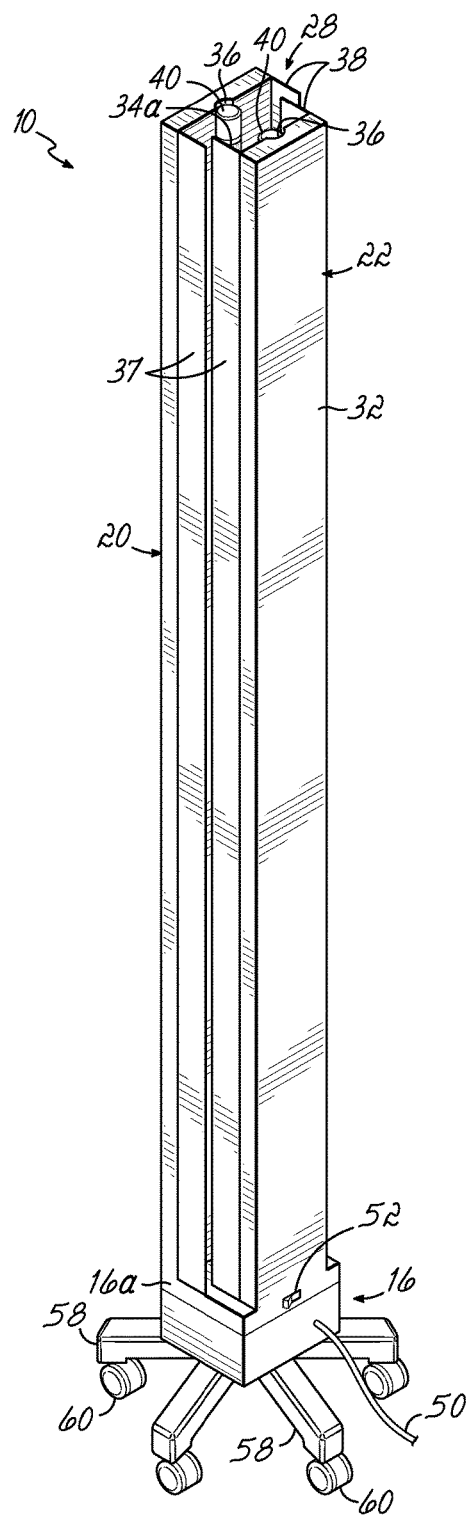
FIG. 1B is a perspective side view of a variation of the curtain sanitizer device of FIG. 1A.
Figure 3B:
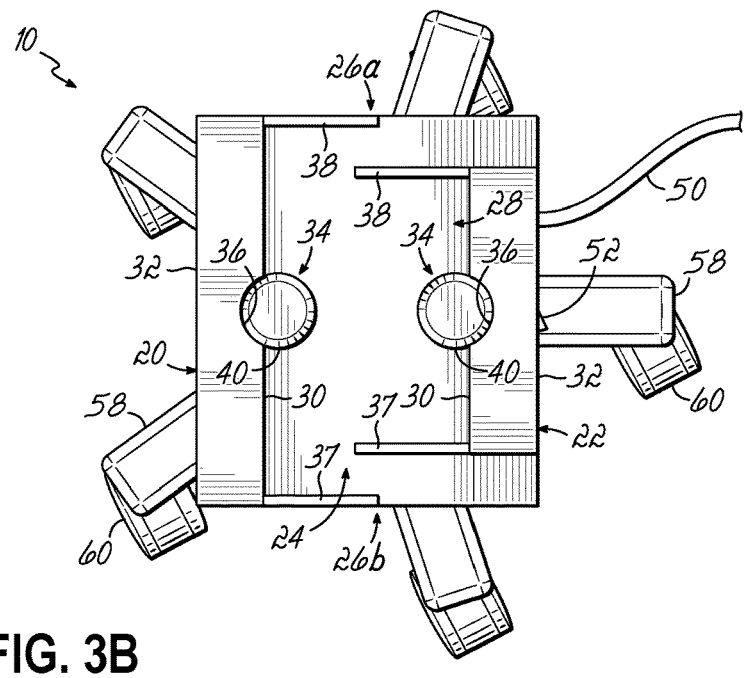
FIG. 3B is top view of the curtain sanitizer device of FIG. 1B.

For example, as shown in FIGS. 1B and 3B, the first wall 20 may be wider than the second wall 22 such that the first and second arms 37, 38 on the opposing second wall 22 generally are situated between the first and second arms 37, 38 of the first wall 20, which provides a generally serpentine curtain channel 24. In this example, at least a portion of the arms 37, 38 of the first wall 20 overlap with at least a portion of the arms 37, 38 of the second wall 22. Other variations and configuration may be contemplated here. In another example, one or more arms 37, 38 may be combined with or replaced with brush seals and the like (not shown) so that the brush seals alone or in combination with the arms 37, 38 act as UV-C radiation safety guards. Other safety measures in line with the aforementioned are contemplated and may be utilized here to help reduce or eliminate UV-C radiation exposure including, for example, automated sensors (not shown) that could shut-off the device 10 if UV-C radiation is detected beyond the safety guards or if one or more safety guards have been removed.

With continuing reference to FIGS. 1, 2, and 3, each wall 20, 22 of the curtain sanitizer device 10 can be secured or attached, directly or indirectly, to the base 16, by means knows in the art. In one example, the walls 20, 22 can be welded, adhesively secured, or the like, to the base. In another example, the walls 20, 22 can be secured or attached to the base 16 by fasteners, including nuts and bolts, screws, nails, dowel rods, and the like. As shown in FIGS. 1 and 2, the walls 20, 22 can be connected together at their proximal ends and therealong via a connecting base piece 16a, by means knows in the art, which can be part of the base 16. While the walls 20, 22 and optional connecting base piece 16a are shown as being one continuous piece or monolithic, it should be understood that each can be separate parts or pieces, which can be secured or attached by means knows in the art, including welding (or the like), adhesives, or via fasteners, such as nuts and bolts, screws, nails, dowel rods, and the like. In addition, it should be understood that the base 16 and connecting base piece 16a can be monolithic or be made of separate parts or pieces and/or the base 16 and one or both of the walls 20, 22 can be monolithic or be made of separate parts or pieces, which can be secured or attached together by means knows in the art. In addition, it should be understood that one or both of the walls 20, 22 can be monolithic or be made of separate parts or pieces, which can be secured or attached together by means knows in the art.

The device 10 further can include a power source 50, e.g., an A/C power cord, suitable for providing electricity to the UV-lights 34 via appropriate electrical connections, as is known to those in the art. In one example, the curtain sanitizer device 10 is configured to be used with a U.S. standard 120 volt outlet. A power cord holder (not shown) may be provided on the curtain sanitizer device 10 or the power cord 50 may be retractable. An on/off switch 52, or button, also may be provided on the curtain sanitizer device 10 to turn the UV-C lights 34 on and off, rather than continuously having to plug and unplug the device 10 for use. In addition, a timing control knob or button (not shown) and/or light intensity control knob or button (not shown), e.g., a dimmer knob, may be provided on the curtain sanitizer device 10, e.g., on the base 16 or wall(s) 20, 22, to control the duration of sanitization and/or the intensity of the light(s) 34.

Other power sources for electrically powering the UV-C lights 34 are contemplated here, including, for example, DC power, a USB or IEEE 1394 receptacle for plugging into a powered USB or IEEE 1394 device, a battery or set of batteries (e.g., LiPo, alkaline, Ni-Cad, etc.), a fuel cell (e.g., using methanol, butane or formic acid), or the like.

The curtain sanitizer device 10 can be stably and vertically positioned on a level surface, such as a floor 54 (FIG. 5), via the base 16. The base 16 can further include a plurality of legs 58 secured thereto on a side opposite that of the walls 20, 22 for more stably positioning the curtain sanitizer device 10 on the floor 54. The legs 58 can be secured to the base 16 by means known in the art. In one example, the legs 58 can be welded (or the like) thereto. In another example, the legs 58 can be secured by fasteners, including nuts and bolts, screws, and the like. Each of the legs 58 further optionally can include a wheel 60 to provide the curtain sanitizer device 10 with a desirable mobility. And one or more of the wheels 60 can have a locking mechanism (not shown), as is known in the art, to help keep the curtain sanitizer device 10 securely situated, in place, at a desired location.

In one embodiment, the device 10, including, for example, the walls 20, 22, base 16, and/or connecting base portion 16a, can be composed of metal(s), polymers, plastics, rubbers, wood, composites, combinations thereof, and the like.

Figure 5:
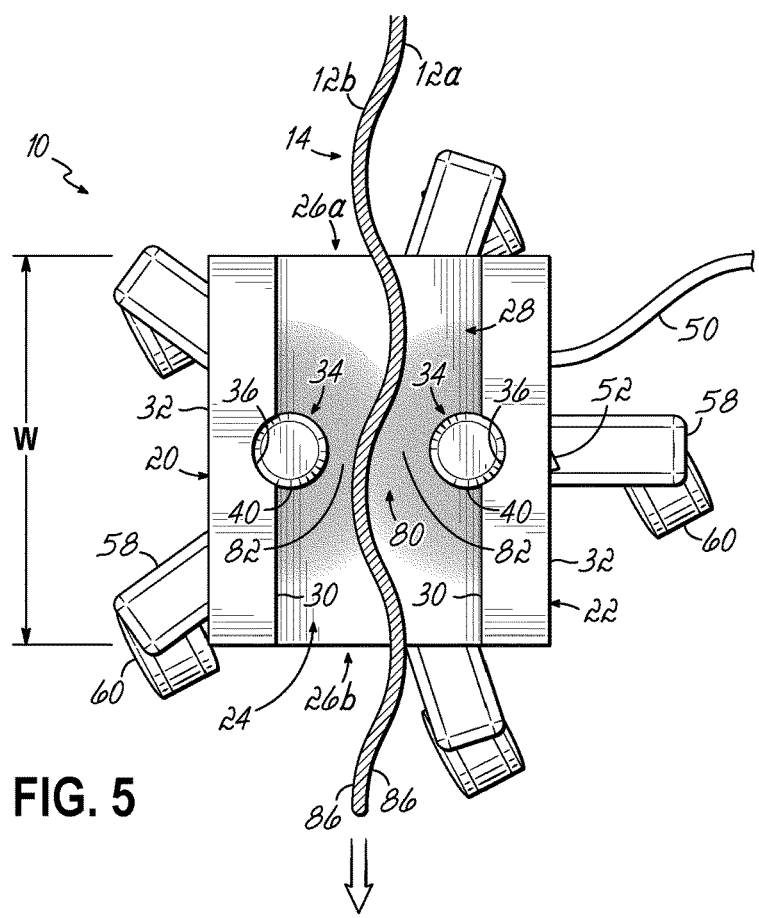
FIG. 5 is a top view of the curtain sanitizer device of FIG. 4 showing, in partial, the privacy curtain of FIG. 4 being sanitized by UV-C light as it moves through the device.
Figure 4:
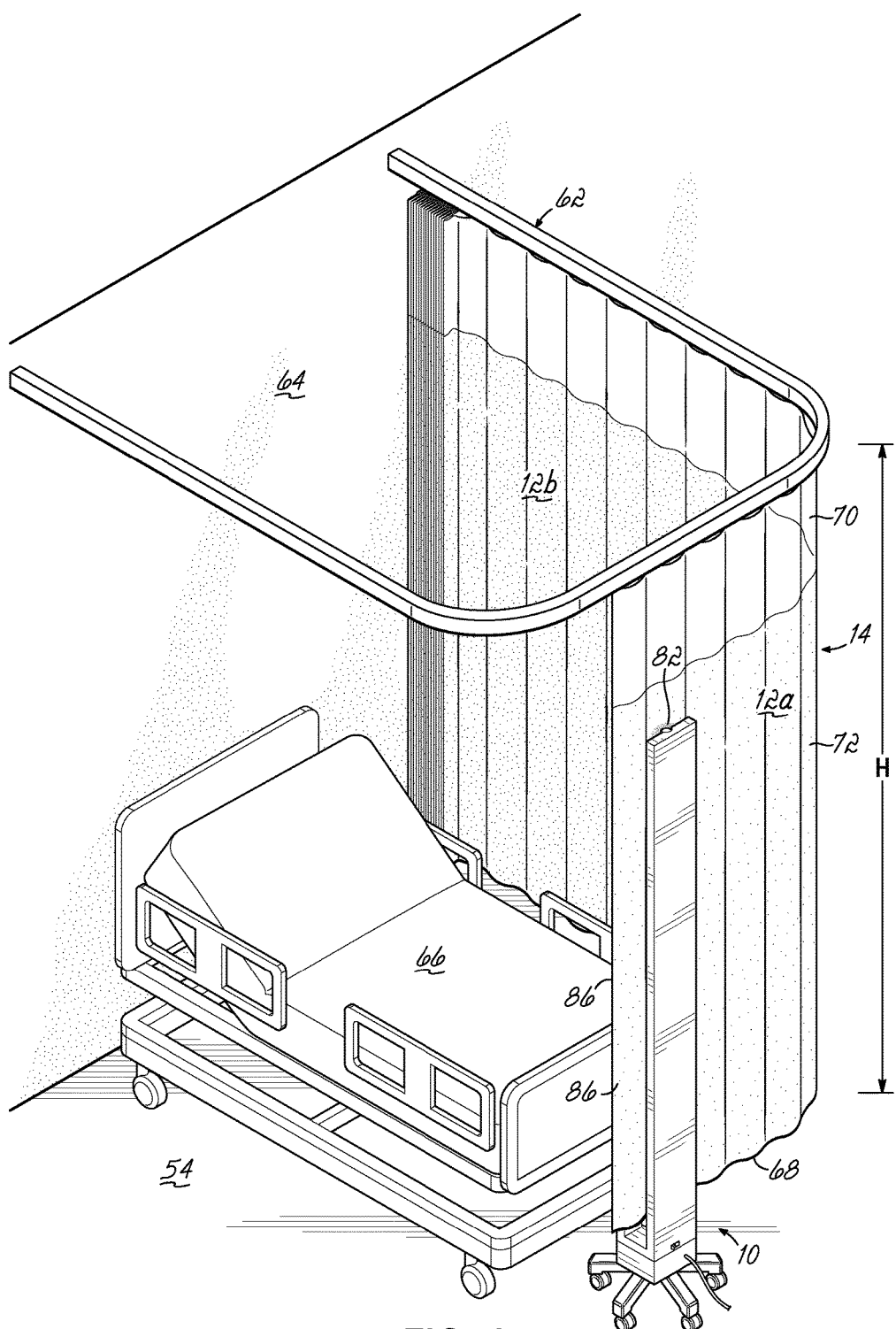
FIG. 4 is a perspective view of the curtain sanitizer device of FIG. 1 showing a privacy curtain being sanitized by the device.

With reference now to FIGS. 4 and 5, curtains 14 that are used in the healthcare setting, e.g., cubicle/privacy curtains, and which may be sanitized by the curtain sanitizer device 10, typically, can be vertically hung and removably secured via a track system 62, as is known in the art. The track system 62 may be securely attached to or hung from a ceiling and/or wall 64 and is configured to allow for easy opening and closing of the curtain 14 by hospital staff, for example. The track system 62, or other curtain hanging system, generally is installed, e.g., oriented and configured, so that the curtain 14, when in an expanded, or in-use, position, can fully or partially encircle, for example, a patient (not shown) situated in a hospital bed 66 so as to provide privacy to that patient. The bottom 68 of the curtain 14 typically rests above the floor 54. The curtain 14 may optionally include an upper mesh, or see through, portion 70 to allow ambient light and fire sprinkler water therethrough. The remainder of the curtain 14, which typically is at least a majority thereof, can include a fabric privacy portion 72, which provides the necessary privacy when in an expanded, or in-use, position. To that end, the fabric privacy portion 72 is generally neither mesh nor of a see through material. In one example, the fabric privacy portion 72 may be composed of fibers that are natural, synthetic, or mixtures thereof and may be woven or non-woven. In one example, substantially all, or all, of the curtain 14 may include the fabric privacy portion 72, e.g. a non-mesh and/or non-see through portion.

To begin the method for sanitizing the curtain 14, the device 10 can be powered on so that the UV-C lights 34 emit radiation. As shown in FIGS. 4 and 5, within the curtain channel 24 is a treatment zone 80 that is primarily located between the UV-C lights 34, and which includes the emitted radiation 82 from the UV-C lights 34. In one example, the device 10 can be positioned at a spot along a designated path of the hung curtain 14 and oriented such that, for example, when the curtain 14 is grabbed at a location above the device 10, the curtain 14 can be manually passed, e.g., pulled or guided, through the curtain channel 24 and the treatment zone 80, between the opposing UV-C lights 34. The UV-C lights 34 direct UV-C radiation 82 on to the side surfaces 12a, 12b, e.g., opposite sides, of the curtain 14 at the treatment zone 80 to simultaneously kill or inactivate harmful microorganisms thereon, thereby sanitizing the curtain 14 and reducing the risk of spreading infectious disease. Alternatively, the device 10 itself can be moved about the hung curtain 14, which is in a generally opened, or in use, position, so that the curtain 14 is passed through the curtain channel 24 and the treatment zone 80, between the opposing UV-C lights 34, to kill or inactivate harmful microorganisms thereon.

The curtain 14 may enter through either side opening 26a, 26b of the curtain channel 24 and pass or be pulled through the treatment zone 80 and curtain channel 24 at a rate that is effective for killing and/or rendering inactive harmful microorganisms. In one example, the intensity of the lights 34 may be adjusted via an optional light intensity control knob or button (not shown). After the curtain 14 is passed completely through the treatment zone 80 and curtain channel 24, at least a treated portion 86 of the side surface 12a, 12b of the curtain 14 is sanitized and the device 10 may be turned off and stored away. In the instance that the device 10 includes UV-C light(s) 34 on only one of the inner surfaces 30, it should be appreciated that the device 10 will need to be re-oriented, e.g., turned 180 degrees, after a first pass of the curtain 14 in order to sanitize at least a portion of the other side surface 12a, 12b of the curtain. Accordingly, in this example, the curtain 14 would need to be passed through the device 10 at least twice to fully sanitize the curtain, i.e., sanitize opposite sides 12a, 12b of the curtain 14.

As shown in FIG. 4, a majority of the height (H) of the curtain 14, which can include a majority of the fabric privacy portion 72 (e.g., a majority of the non-mesh portion), can be passed through the treatment zone 80 and sanitized by the UV-C lights 34. In this manner, the area(s) most prone, for example, to contact by unsanitary hands can be sanitized. In another example, all of the fabric privacy portion 72 of the curtain 14, can be passed through the treatment zone 80 and sanitized by the UV-C lights 34. Again, it should be understood that the manufactured length of the walls 20, 22, for example, and, thus, the overall height of the device 10 may be adjusted accordingly to correspond to the curtain height (H) needed to desirably sanitize the target curtain(s) 14. It should be readily understand by one skilled in the art that devices 10A and 10B can sanitize hung curtains 14 in the same, or similar, manner as above described with respect to device 10.

With reference now to FIGS. 6, 7, 8, and 8A, in accordance with another embodiment of the invention, curtain sanitizer device 100, which is a variation of curtain sanitizer device 10, is shown including a plurality of curtain guides 102, e.g., rotatable wheels, which are oriented to mechanically cooperate and guide the curtain 14 (See FIG. 9) through the curtain channel 24 and treatment zone 80. The wheels 102 can be secured or attached to the walls 20, 22 by means in the art, such as support brackets 104 or the like. In this embodiment, a total of four pairs of wheels 102a, 102b, 102c, and 102d are provided on the walls 20, 22, with two pairs 102a, 102b and 102c, 102d being provided on each inner surface 30. One pair of wheels 102a, 102c on each inner surface 30 is situated approximate the open top end 28 and the other pair 102b, 102d is situated approximate the base 16. The wheels 102 in each pair 102a-d are situated on opposite sides of the UV-C light 34 and are horizontally aligned with one another. Each wheel 102 in each pair of wheels 102a-d corresponds with and is situated in a spaced apart and opposing relationship to another wheel 102 on the opposing inner surface 30 so that the opposing pairs of wheels 102a, 102c and 102b, 102d are aligned with another and provide a gap 108 that receives the curtain 14.

Figure 9:
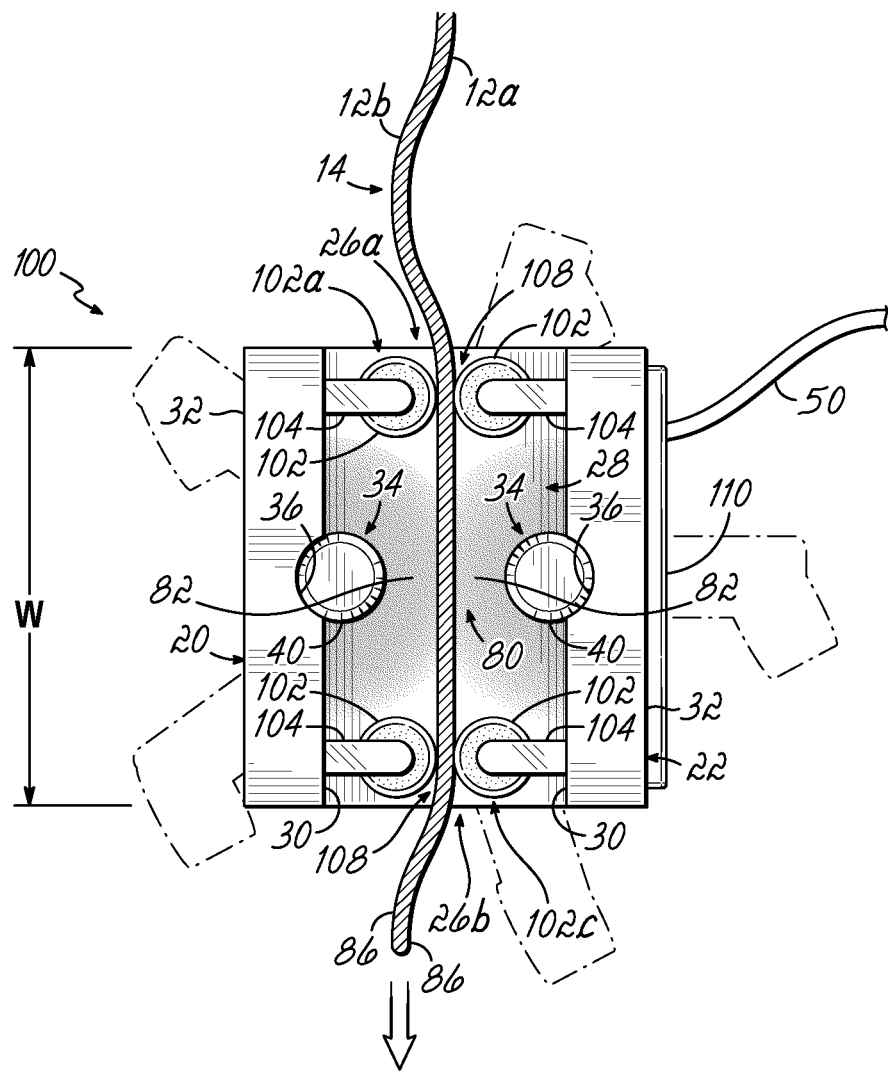
FIG. 9 is a top view of the curtain sanitizer device of FIG. 6 showing, in partial, a privacy curtain being sanitized by UV-C light as it moves through the device.
Figure 10:
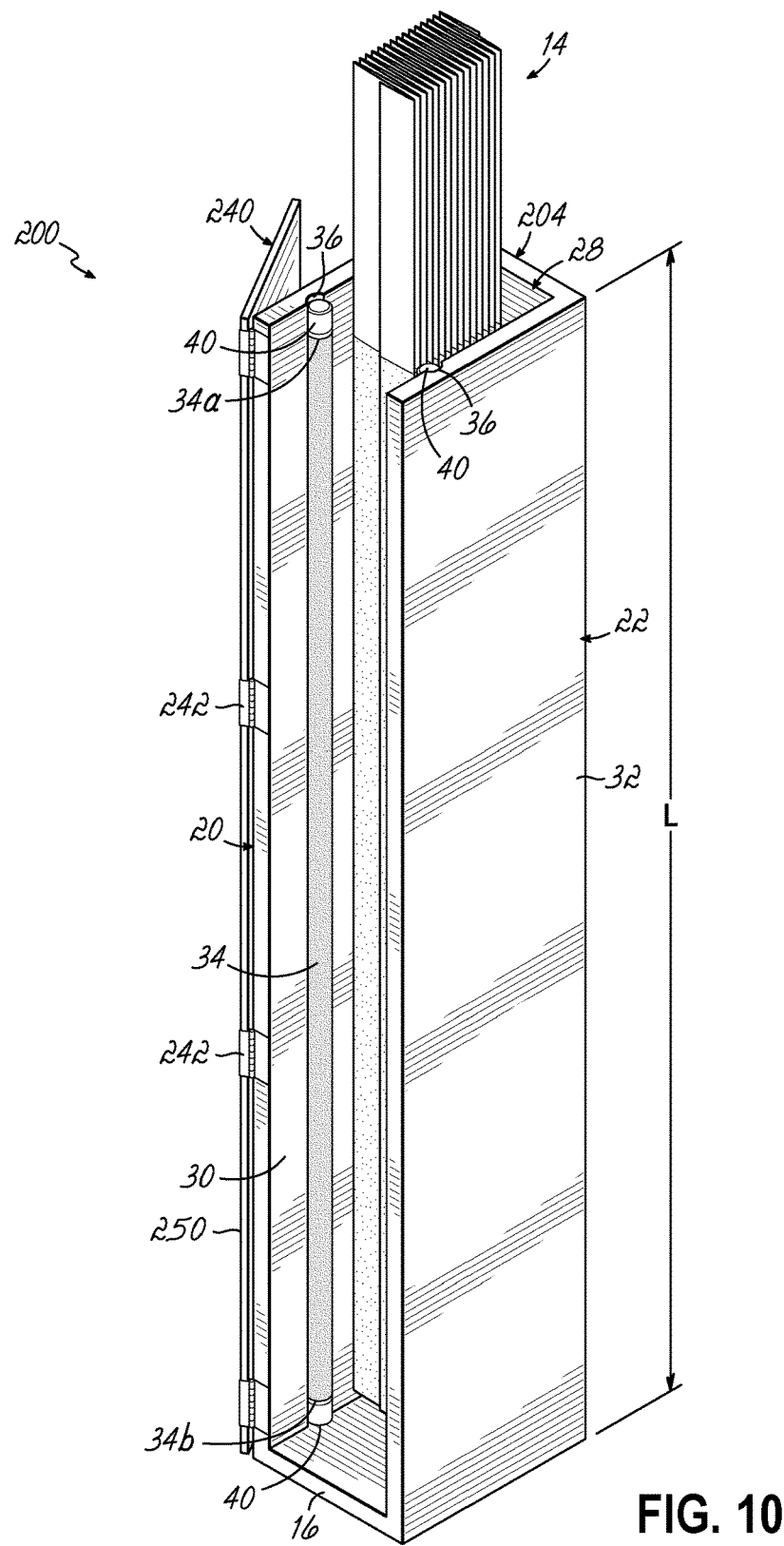
FIG. 10 is a perspective side view of a curtain sanitizer device in accordance with another embodiment of the present invention, in an opened position, with a privacy curtain in a fully retracted, or non-use, position.
Figure 11:
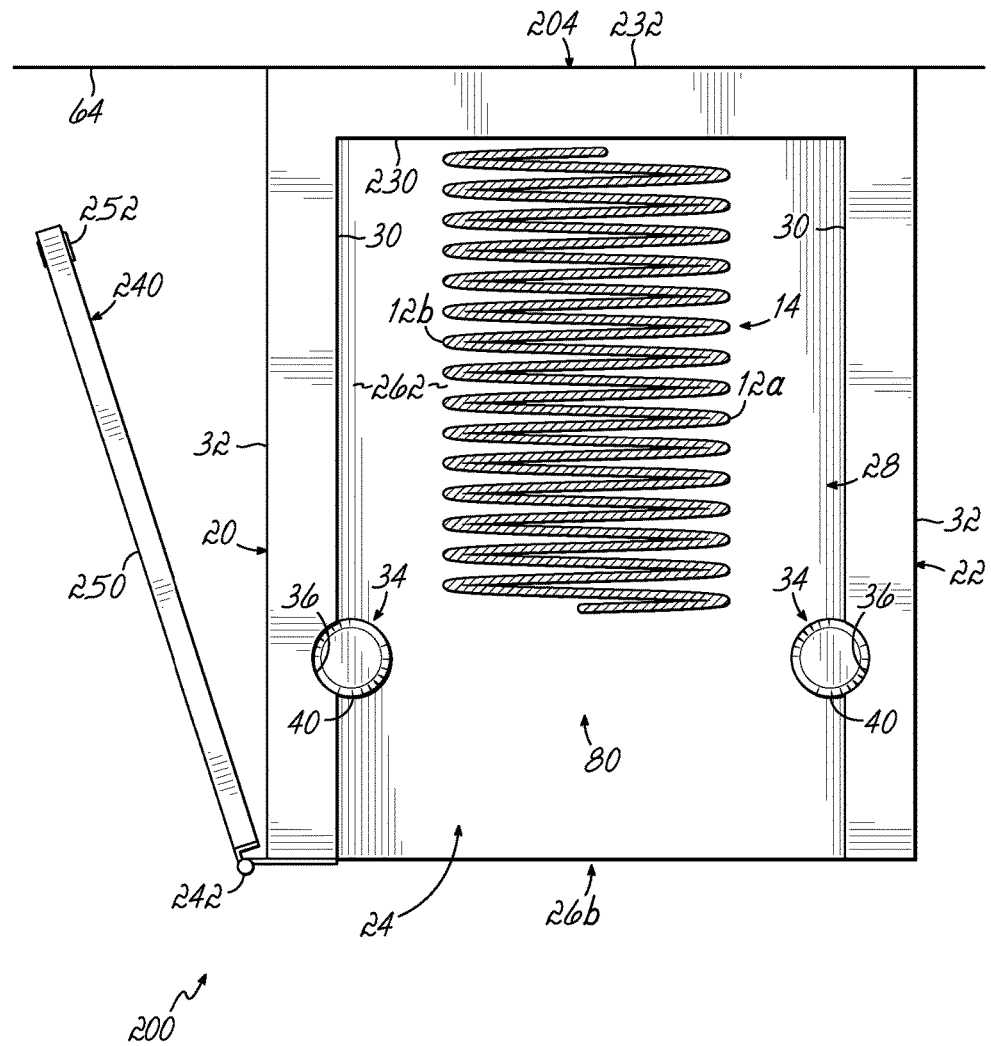
FIG. 11 is a top view of the curtain sanitizer device of FIG. 10.
Figure 12:
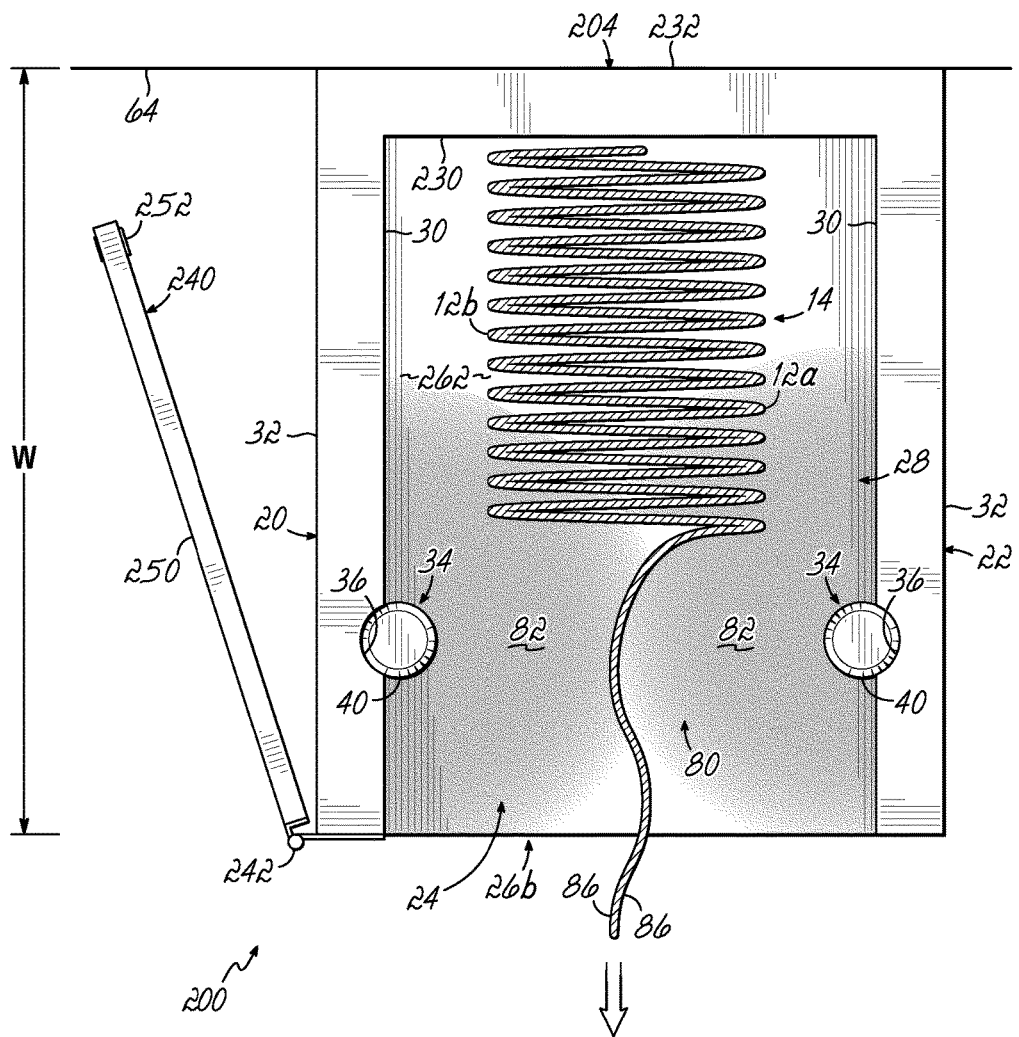
FIG. 12 is a top view of the curtain sanitizer device of FIG. 10 showing the privacy curtain being sanitized by UV-C light as it moves through the device.
Figure 13:
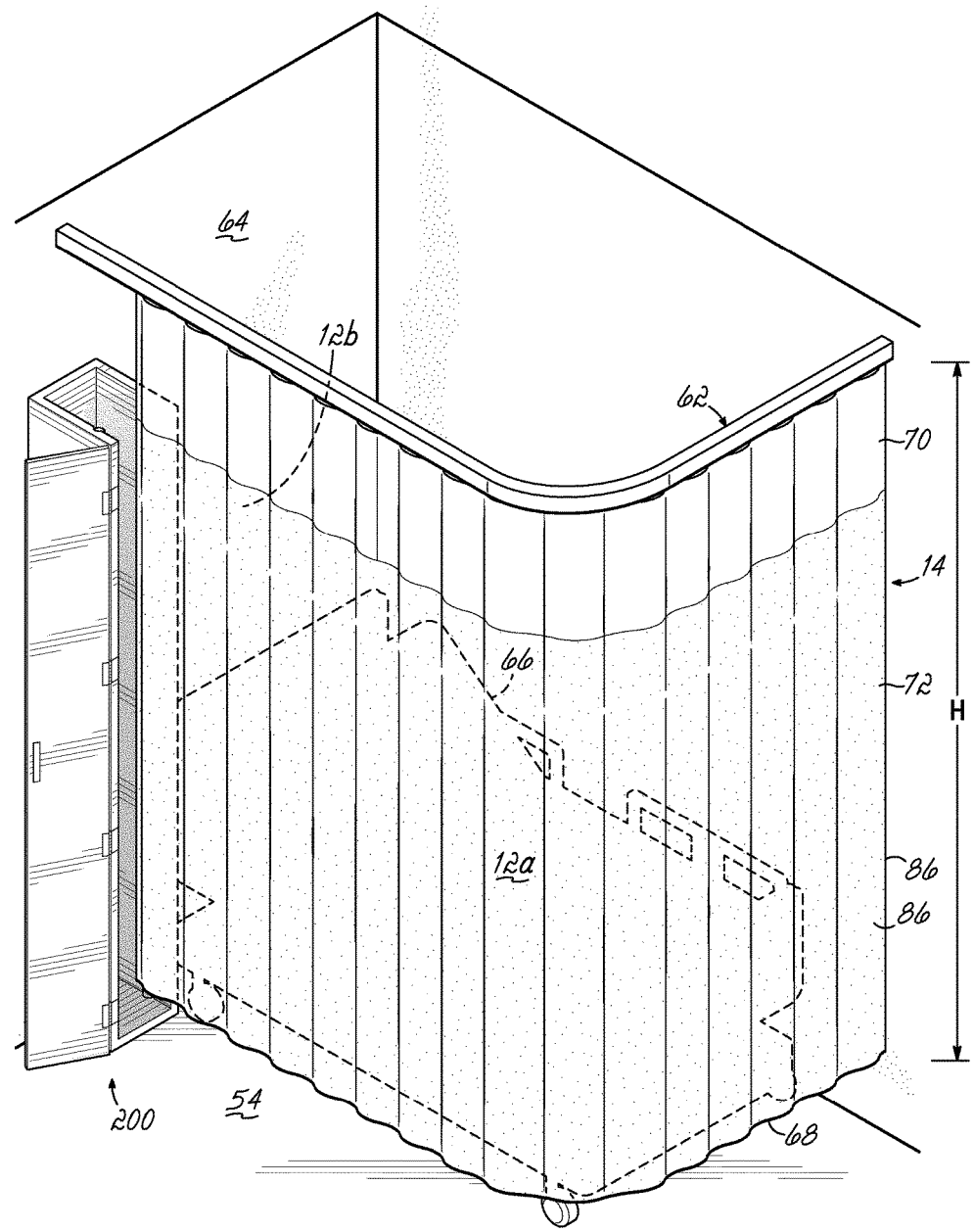
FIG. 13 a perspective side view of the curtain sanitizer device of FIG. 10 with the privacy curtain in a fully expanded, or in-use, position.
Figure 14:
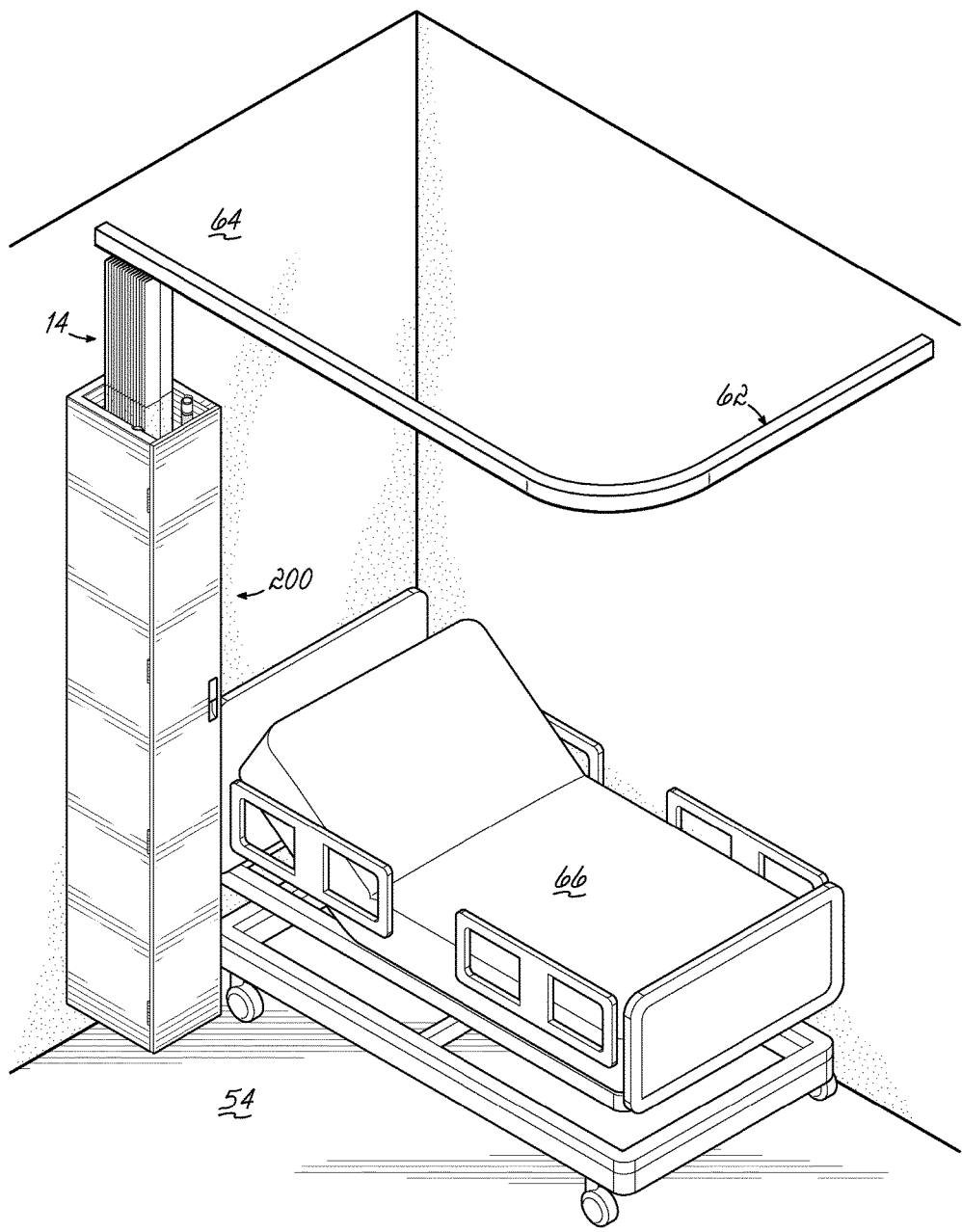
FIG. 14 is a perspective side view of the curtain sanitizer device of FIG. 10, in a closed position, with the curtain in a fully retracted or non-use position.

In one example, the wheels 102 are motorized. For example, the pairs of wheels 102a-d, or each wheel 102 individually, may be controlled by a single motor 109. In another example, as shown, each pair 102a-d is controlled by its own motor 109. In one example, the on/off switch 52 controls the rotation of the wheels 102. In another example, one or more separate on/off switches 52 controls rotation of the wheels 102. In another example, the speed of rotation of the wheels 102 can be controlled, such as by a knob or button. In another example, the wheels 102 may be installed with a hinge (not shown) so that each can have a clear open or in-use position and a closed or non-use position. In another example, the wheels 102 are immovable, i.e., stationary. Still yet, in another example, the wheels 102 may be replaced altogether with one or more nubs or protrusions (not shown) of any desired configuration, shape, and/or size that extends in a direction away from the inner surface 30 of each wall 20, 22 and which act as curtain guides for the hung curtain 14 (FIG. 9).

In another example, instead of four pairs of wheels 102a-d, only two complementary pairs of wheels 102a, 102c are provided, and these two pairs 102a, 102c may be situated intermediate the base 16 and the top open end 28. In yet another example, only one wheel 102 is provided from each of only two complementary pairs 102a, 102c of wheels, thereby providing one wheel 102 on the inner surface 30 of one wall 20 and a corresponding wheel 102 on the inner surface 30 on the other wall 22. In one example, the one wheel 102 and the corresponding wheel 102 can extend generally the length (L) of each wall 20, 22 defining an elongated roller (not shown). That is, the size and/or width of each wheel 102 can vary. It also should be understood that the number of wheels 102 or pairs of wheels 102a-d and/or the positioning thereof at different locations along the length (L) of the walls 20, 22 may vary while still accomplishing mechanically guiding the curtain 14 through the curtain channel 24 and treatment zone 80. The wheels 102 can be biased, e.g., spring biased, to accommodate different thicknesses in curtains 14 and to help provide traction for moving the curtain 14 through the curtain channel 24. In another example, the motorized wheels 102 may be configured to automatically rotate only upon contact with the curtain 14 and may rotate in either direction. The wheels 102 may be composed of various materials, such as rubber, silicone, or the like, that also can provide for desirable traction with the curtain fabric to assist with moving the curtain 14 through the curtain channel 24.

Figure 6:
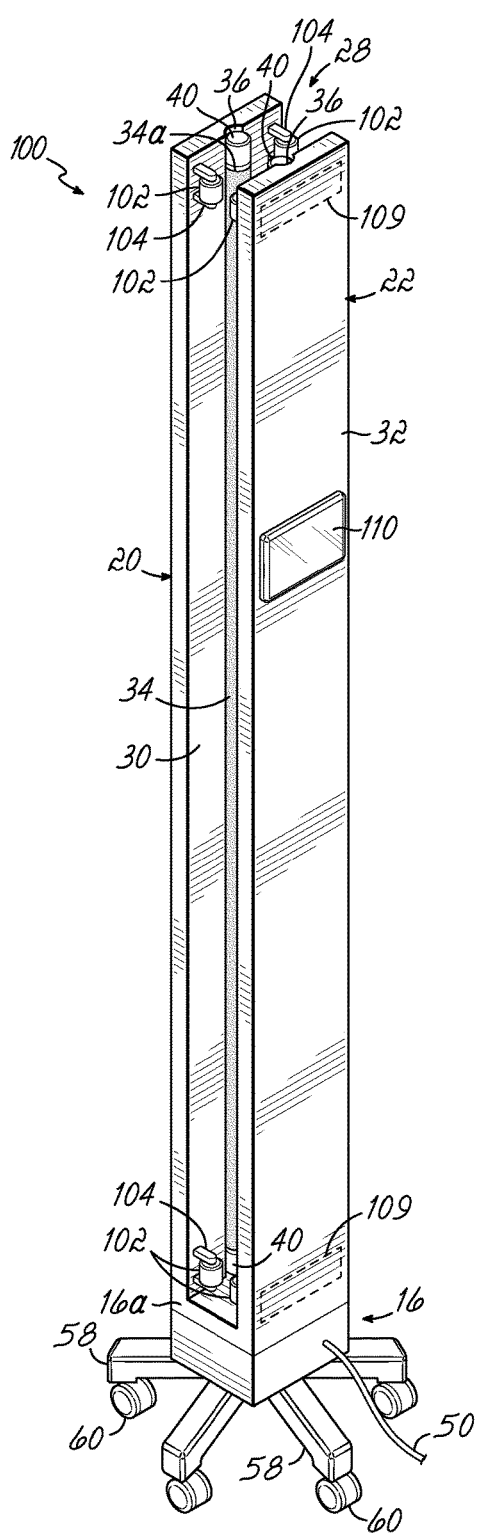
FIG. 6 is a perspective side view of a curtain sanitizer device in accordance with another embodiment of the present invention.
Figure 6A:
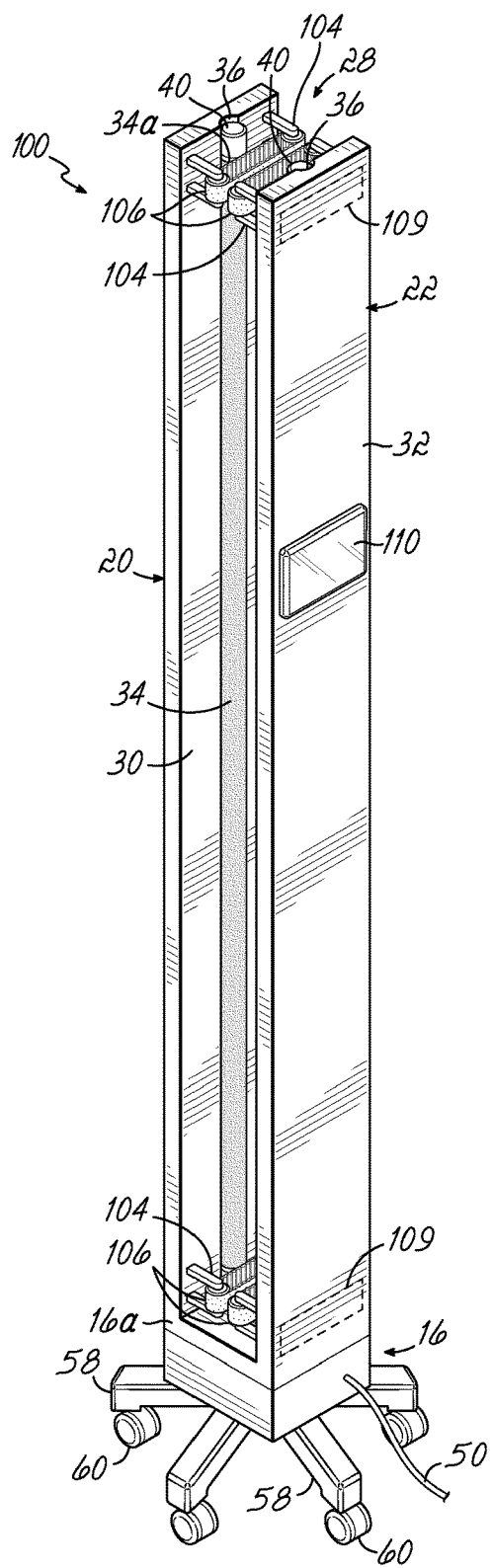
FIG. 6A is a perspective side view of the curtain sanitizer device of FIG. 6 showing a conveyor belt configuration for moving a hung curtain through the curtain cannel.
Figure 8:
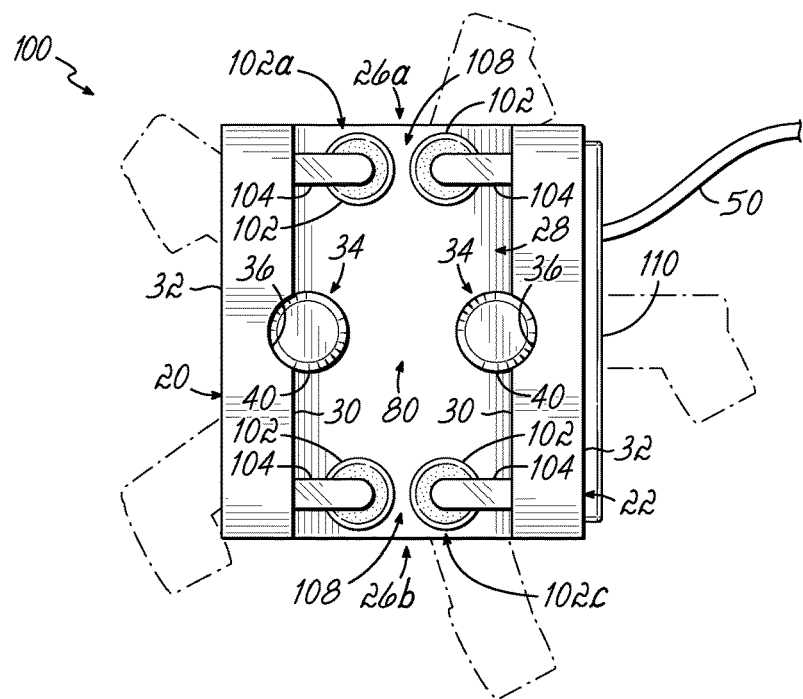
FIG. 8 is a top view of the curtain sanitizer device of FIG. 6.
Figure 8A:
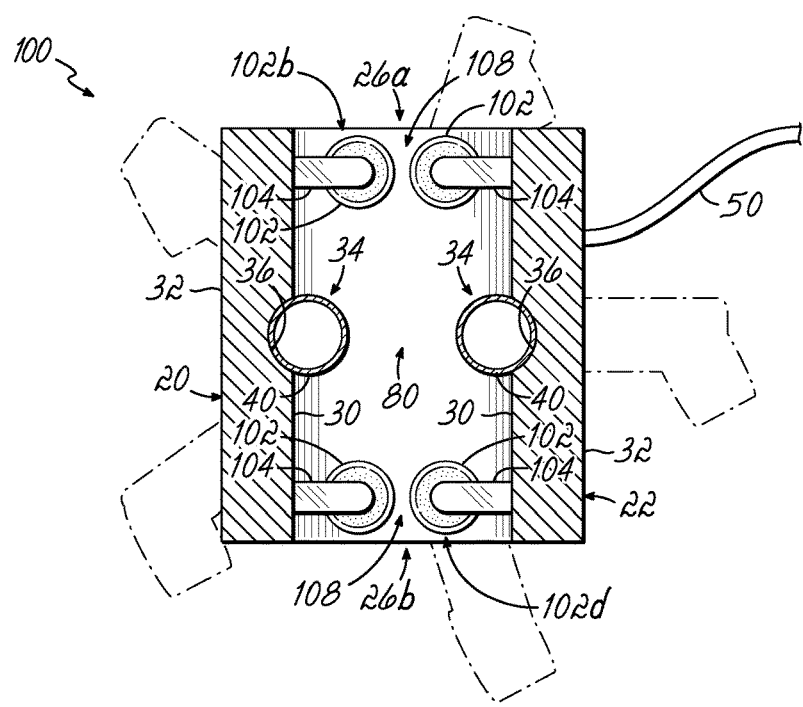
FIG. 8A is a cross-sectional view of the curtain sanitizer device of FIG. 6 taken along lines 8A-8A.
Figure 8B:
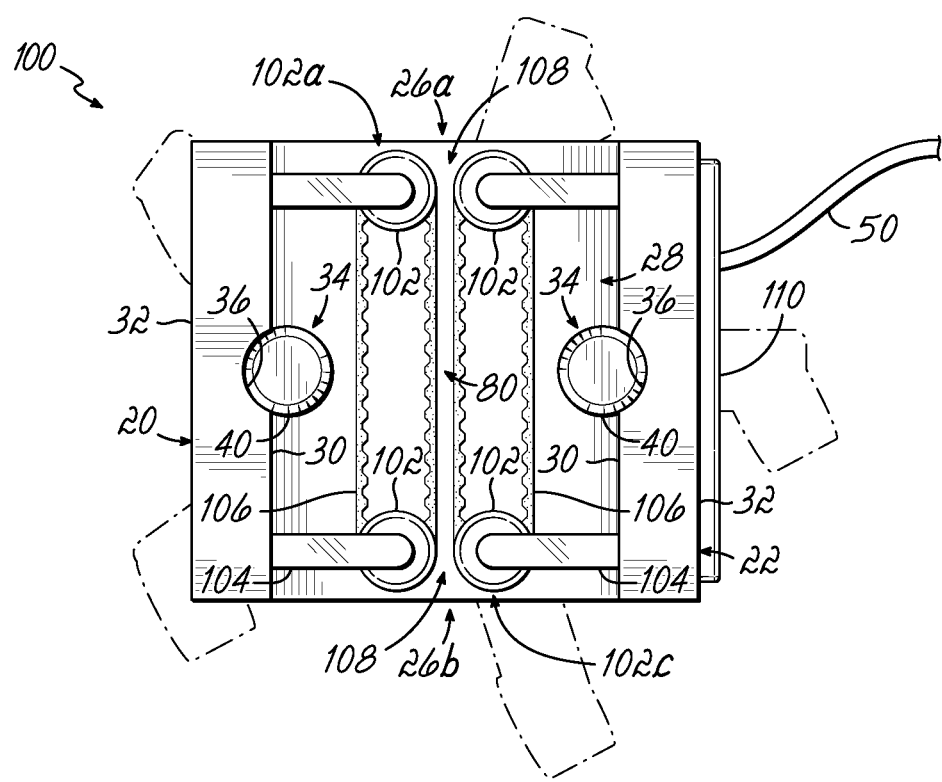
FIG. 8B is top view of the curtain sanitizer device of FIG. 6A.

In another embodiment, as shown in FIGS. 6A and 8B, each of the pairs of wheels 102a-d of device 100A can be provided with a belt 106 that can cooperate with and help convey or move the hung curtain 14 through the curtain channel 24 and treatment zone 80 when one or more of the wheels 102 are motorized and the device 100 is in use. In another example, the belt 106 may be replaced by a track or the like. The track or belt 106 may be composed of various materials, such as rubber, silicone, or the like, that can provide for desirable traction with the curtain fabric to assist with moving the curtain 14 through the curtain channel 24. In one example, the wheels 102 and track or belt 106 can be configured to be biased, e.g., spring biased, to accommodate different thicknesses in curtains 14 and to help provide traction for moving the curtain 14 through the curtain channel 24.

Figure 7:
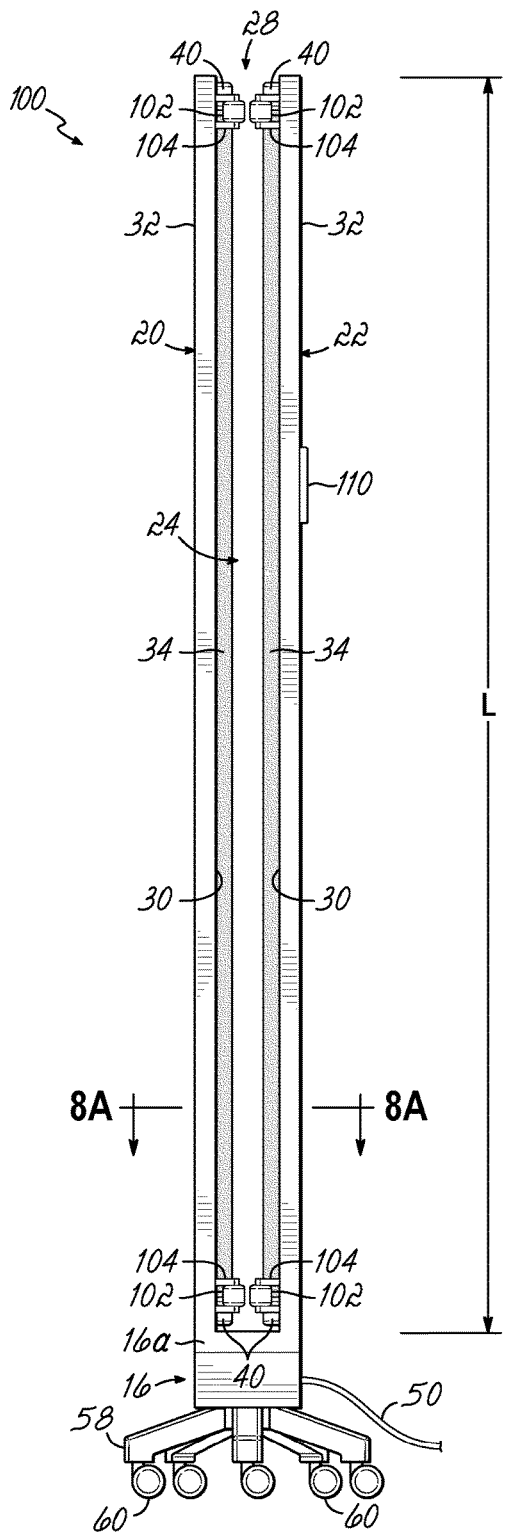
FIG. 7 is a side elevational view of the curtain sanitizer device of FIG. 6.

With further reference to FIGS. 6 and 7, the curtain sanitizer device 100 also can include a touch screen interface 110, which can be associated with a control system including a processor configured to execute computer-readable instructions, as is known to those skilled in the art, to perform at least one sanitizing operation. The computer-readable instructions may be stored in a non-transitory computer storage medium, such as a computer memory in communication with the processor. The touch screen interface 110, such as via user input, may perform any or all of the above identified functions associated with operation of the device 100, including, but not limited, to turning the device 100 on or off, turning the UV-C lights 34 on or off, adjusting the intensity or controlling the duration of the UV-C lights 34, turning the rotation of motorized wheels 102 on or off, and adjusting the speed of rotation of motorized wheels 102 thereby allowing the user to change the speed that the curtain 14 passes through the treatment zone 80, etc. The touch screen 110 also may identify that the device 100 is ready for operation, currently operating, or that sanitizing is complete. In one example, a sanitizing time can be set, via the touch screen 110, so as to deliver the appropriate amount of UV energy needed to kill or render inactive a range of target microorganisms. And as discussed above, the device 100, 100A may be provided with UV-C radiation safety guards, e.g. arms 37, 38 (See, e.g., FIG. 1A), brush seals, and the like.

With further reference to FIG. 9, to sanitize at least a portion of the curtain 14 in place, the device 100 can be powered on so that the UV-C lights 34 emit UV-C radiation 82 and optional motorized wheels 102 can rotate. Within the curtain channel is the treatment zone 80 that is primarily located between the UV-C lights 34, and which includes the emitted radiation 82 from the UV-C lights 34. In one example, the device 100 can be positioned at a spot along the designated path of the hung curtain 14 and oriented such that, for example, the curtain 14 can be grabbed at a location above the device 100 and passed, e.g., pulled or guided, through or between the gaps 108 in the wheels 102 and through the curtain channel 24 and the treatment zone 80, between the opposing UV-C lights 34, to kill or inactivate harmful microorganisms thereon, thereby simultaneously sanitizing at least the targeted portion 86 of opposite side surfaces 12a, 12b of the curtain 14 and reducing the risk of spreading infectious disease.

Concerning the motorized wheels 102, after the curtain 14 is manually fed into the gaps 108 therebetween, the curtain 14 can be automatically rolled or passed through the curtain channel 24 and the treatment zone 80, between the opposing UV-C lights 34, to kill or inactivate harmful microorganisms thereon. In one example, the intensity of the lights 34 may be adjusted via touch screen interface 110. If the wheels 102 are non-motorized and rotate freely in either direction, the curtain 14 may enter through either side opening 26a, 26b of the curtain channel 24 and pass or be pulled through the treatment zone 80 at a rate that is effective for killing and/or rendering inactive harmful microorganisms. However, if the wheels 102 are motorized, as is shown, unless the direction of rotation of the wheels 102 can be reversed, which is contemplated here, there will be an enter side and an exit side for the curtain 12 as it passes into and out of the curtain channel 24 and treatment zone 80. And again, in the instance that the device 100 includes UV-C light(s) 34 on only one of the inner surfaces 30, it should be appreciated that the device 100 will need to be re-oriented, e.g., turned 180 degrees, after a first pass of the curtain 14 in order to sanitize at least a portion of the other side surface 12a, 12b of the curtain 14.

After the curtain 14 is passed completely through the treatment zone 80 and curtain channel 24, at least targeted portion 86 of the curtain 14 is sanitized and the device 100, including the UV-C light 34 and any motorized wheels 102, for example, may be turned manually or automatically off, and the device 100 stored away. In one example, a majority of the height (H) of the curtain 14, which can include a majority of the fabric privacy portion 72 (e.g., a majority of the non-mesh portion), can be passed through the treatment zone 80 and sanitized by the UV-C lights 34. In this manner, the area(s) most prone to contact by unsanitary hands can be sanitized. In another example, all of the fabric privacy portion 72 of the curtain 14 can be passed through the treatment zone 80 and sanitized by the UV-C lights 34. It should be readily understand by one skilled in the art that device 100A can sanitize hung curtains 14 in the same, or similar, manner as above described with respect to device 100.

With reference now to FIGS. 10-14 and in accordance with another embodiment of the invention, a curtain sanitizer device 200 is shown that is configured to be permanently or removably mounted to wall 64, or other solid surface, by means known in the art, to define a wall mounted unit and which similarly utilizes UV-C radiation to reduce the risk of spreading infectious diseases through direct contact with curtains 14, e.g., privacy curtains, such as those used in healthcare settings. The device 200 includes base 16, which here is optional, and spaced apart and opposing first and second elongated walls 20, 22 extending in a direction generally perpendicularly away from the base 16, or extending in parallel relation to one another if the base 16 is not present. The first and second elongated walls 20, 22 can be joined or connected together by a back wall 204, by means known in the art, including welding, adhesives, and/or via fasteners, such as nuts and bolts, screws, nails, dowel rods, and the like. That is, one side opening 26a, 26b of the curtain channel of the curtain sanitizer device 10, 100 (See FIGS. 1 and 6) now is generally closed off by the back wall 204. In one example, the back wall 204 is elongated and joins the first and second walls 20, 22 together along back side edges thereof forming a generally elongated U-shaped configuration.

The back wall 204 includes an inner and an outer surface 230 and 232, with the outer surface 232 of the back wall 204 able to be permanently or removably mounted to the wall 64. An optional front door 240 can be joined or connected to the first or second wall 20, 22 at one or more locations, such as along a front side edge, by means known in the art, including hinges 242 and the like, to allow the front door 240 to be opened and closed. An inner surface 250 of the front door 240, when the front door 240 is closed, is in opposing relationship to the inner surface 230 of the back wall 204. Although the length can vary, in this embodiment, the length of the back wall 204 and front door 240 is the same as that of the first and second walls 20, 22. A knob or handle 252, including associated hardware and/or locking mechanisms, as is known in the art, may be provided on the front door 240 or associated with the front door 240 and a cooperating first or second wall 20, 22 to facilitate opening and closing and/or to keep the front door 240 closed and/or locked when the device 200 is not in use.

The top or terminal end of each of the walls 20, 22, 204 and the optional front door 240 (when closed), define the open top or distal end 28, which can be generally rectangular in shape, although other shapes and configurations are contemplated. The optional front door 240, when opened, provides one elongated side opening 26a or 26b to the curtain channel 24 and gives access to an interior of the device 200. The side opening 26a defines an exit and entrance to the curtain channel 24. The device 200 optionally may be provided with cooperating UV-C radiation safety guards, e.g., one of the arms 37, 38 (See, e.g., FIG. 1A) and/or brush seals, and the like, such as horizontally along the inner surface 30 of each first and second wall 20, 22 adjacent a front side edge thereof so as reduce or eliminate any potential UV-C radiation exposure to users and bystanders when the device is in use. In one example, only one arm 37 and/or brush seal may be provided extending from each wall 20, 22, such as adjacent a front side edge thereof. The safety guards cooperating to provide the elongated side opening 26a or 26b to the curtain channel 24 and to give access to the interior of the device 200. The side opening 26a defining an exit and entrance to the curtain channel 24.

The first and second walls 20, 22 can include relatively flat and opposing inner surfaces 30 and relatively flat outer surfaces 32. The inner surface 30 can further include the optional recessed channel 36 extending along about the length (L) of the first and second walls 20, 22 for receiving the UV-C light 34. In this embodiment, the optional recessed channel 36 and/or UV-C light 34 can be situated offset from a central position and away from the back wall 204 towards or approximate the side opening 26a to the curtain channel. The offset location of the recessed channel 36 and/or the UV-C light 34 provides a curtain housing area 262 between the inner surface 230 of the back wall 204 and the UV-C lights 34 so that the curtain 14 can be stored in the device 200 when in a retracted, or non-use, position. To that end, the device 200 can be removably or permanently situated on the wall 64 and along the designated path of the curtain 14, with the device 200 being oriented such that, for example, the curtain 14 can be stored therein and then pulled therethrough for sanitizing the side surfaces 12a, 12b of the curtain 14.

As discussed above, it should be appreciated that variations of the size, shape, configuration, and/or number of the lights 34 and any corresponding recessed channel 36, if so desired, can be contemplated here. In addition, the UV-C light 34, or a plurality of lights, may extend approximately the length (L) of the wall 20, 22 or less than the length (L) of the wall 20, 22. And the manufactured length (L) of the wall(s) 20, 22 and, thus, the overall height of the device 200 may be adjusted accordingly to correspond to the height needed to desirably sanitize the target curtain(s) 14.

The device 200 can include a power source 50, e.g., an A/C power cord like that shown in FIG. 1, suitable for providing electricity to the UV-lights 34 via appropriate electrical connections, as is known to those in the art. In another example, on/off switch 52, like that shown in FIG. 1, may be provided on the curtain sanitizer device 200 to turn the UV-C lights 34 on and off, rather than continuously having to plug and unplug the device 200 for use. The device 200 also may be electrically hardwired into the wall, as is known in the art, to provide electricity to the device 200, and a corresponding on/off switch or button, e.g., a wall switch (not shown), may be provided on the wall 64 or on the device 200 to power the device 200 on and off. In addition, a light intensity control knob or button (not shown), e.g., a dimmer knob, may be provided on the curtain sanitizer device 200, e.g., on the base 16 or wall(s) 20, 22, to control the duration of sanitization and/or the intensity of the light(s) 34. Touch screen interface 110, like that shown and described in FIG. 6, also may be provided on the wall 64 or on the device 200. Other power sources for electrically powering the UV-C lights 34, as discussed above, are contemplated here.

With further reference to FIGS. 10-14, to sanitize the curtain 14 in place, the device 200 can be powered on so that the UV-C lights 34 emit UV-C radiation 82. Within the curtain channel 24 is the treatment zone 80 that is primarily located between the UV-C lights 34, and which includes the emitted radiation 82 from the UV-C lights 34. The optional front door 240 can be opened and the retracted curtain 14 can be grabbed at a location, for example, above the device 200 and manually pulled or guided through the treatment zone 80, between the opposing UV-C lights 34, and out the side opening 26a of the curtain channel 24 to kill or inactivate harmful microorganisms thereon, thereby simultaneously sanitizing the targeted portion 86 of opposite side surfaces 12a, 12b of the curtain 14 and reducing the risk of spreading infectious disease. In one example, the hung curtain 14 may be pulled all the way out from within the interior of the device 200, and the front door 240 may be closed.

After the curtain 14 is passed through the treatment zone 80 and out the curtain channel 24, at least the targeted portion 86 of the hung curtain 14 is sanitized and the device 200, including the UV-C light 34, may be manually or automatically turned off. When the curtain 14 is no longer needed, the curtain 14 may be retracted, or pulled or pushed, back into the curtain housing area 262, until needed again, and the front door 240 closed. Then, the sanitizing method may be repeated, as needed. In one example, a majority of the height (H) of the curtain 14, which can include a majority of the fabric privacy portion 72 (e.g., a majority of the non-mesh portion), can be passed through the treatment zone 80 and sanitized by the UV-C lights 34. In this manner, the area(s) most prone to contact by unsanitary hands can be sanitized. In another example, all of the fabric privacy portion 72 of the curtain 14 can be passed through the treatment zone 80 and sanitized by the UV-C lights 34.

Again, the UV-C light 34 can be utilized to kill or inactivate bacteria, molds, protozoa, yeasts, and viruses on the surfaces 12a, 12b of hung curtains 14, such as privacy curtains used in healthcare settings, including those microorganisms that can cause and lead to the spread of infectious diseases. In one example, the curtain sanitizer device 10, 100, 200, with its UV-C light 34 can desirably kill and/or render inactive over 90% of harmful microorganisms on the surface 12a, 12b of the curtain 14. In another example, the device 10, 100, 200 can desirably kill and/or render inactive over 95% of harmful microorganisms. In another example, the device 10, 100, 200 can desirably kill and/or render inactive over 99% of harmful microorganisms. In yet another example, the device 10, 100, 200 can desirably kill and/or render inactive over 99.9% of harmful microorganisms.

As is understood in the art, desirably sanitizing an object, e.g., the curtain 14, depends on numerous factors, including, but not limited to the emission power of the UV-C light 34, the projection angle of the UV-C light emitted 82, the speed or length of time that the curtain 14 is exposed to the UV-C radiation 82, the distance of the curtain 14 from the UV-C light 34, and the target microorganism(s). The overall radiation intensity, which is generally defined by the unit milliwatts/cm$^2$, that the curtain 14 will be subjected or exposed to when a particular device, such as the curtain sanitizer device 10, 100, 200, is used to sanitize can be calculated by means and methods known in the art. For example, taking into consideration various factors, including the targeted microorganism, emission power of the UV-C light 34, distance from the UV-C light 34, etc., one can determine the length of time the curtain 14 must be exposed to the UV-C light 34 and, thus, the rate or speed that the curtain 34 can be passed through the treatment zone 80 to be sanitized. Notably, different organisms require different amounts of radiation exposure to kill or render inactive. Tables of energy for deactivation of a variety of microorganisms, e.g., the amount of UV energy levels at 254 nanometer units wavelength in microwatt-seconds per square centimeter required for 99.9% destruction of various organisms, is readily available to those skilled in the art. Generally, speaking slower curtain speeds will allow the device 10, 100, 200 to kill or inactivate a wider variety of microorganisms.

The following is a list of microorganisms that can be killed or inactivated by embodiments of the present invention emitting UV-C radiation, and some of the diseases they cause: Bacteriophage (*E. Coli*), HIV, Infectious Hepatitis, Influenza (Flu), Poliovirus-Poliomyelitis, Tobacco mosaic, Rotovirus, S *Bacillus anthracis* (Anthrax), *Bacillus magaterium* sp. (Spores), *Bacillus magaterium* sp. (Veg), *Bacillus paratyphusus, Bacillus subtilus* spores, *Bacillus subtilis, Clostridium tetani* (Tetanus/Lockjaw), *Clostridium difficile, Corynebacterium diphtheriae* (Diphtheria), *Eberthella typosa, Escherichia Coli* (*E. Coli*), *Leptospira Canicoal*-infections (Jaundice), Methicillin-resistant *Staphylococcus Aureus* (MRSA) *Micrococcus candidus, Micrococcus spheroids, Mycobacterium tuberculosis* (Tuberculosis), *Neisseria catarrhalis, Phtomomnas aeruginosa, Pseudomonas fluorescens, Salmonella enteritidis, Salmonella paratyphi* (Enteic Fever), *Salmonella typhosa* (Typhoid Fever), *Salmonella typhimurium, Sarcina lutea, Serratia marcescens, Shigella dysenteriae* (Dysentery), *Shigella flexneri* (Dysentery), *Shigella paradysenteriae, Spirillum rubrum, Staphylococcus Albus* (Staph), *Staphylococcus Aureus* (Staph), *Streptococcus hemolyticus, Streptococcus lactis, Streptococcus viridians, Vibrio comma*-(Cholera), and mold spores including *Aspergillius Flavis, Aspergillius glaucus, Aspergillius niger, Mucor racemosus* A, *Mucor racemosus* B, *Oospora lactis, Penicillium expansum, Penicillium roqueforti, Penicillium digitatum*, and *Rhisophus nigricans*. The effectiveness of aspects of this invention to kill or render inactive harmful microorganisms will be apparent to those of skill in the art. With the curtain sanitizer device and method, in one example, substantially all, or all, of the curtain can be sanitized in less than one minute. And within this time period, the curtain can be sanitized against harmful microorganisms, such as rotavirus, *E. coli*, and *salmonella*, which can spread infectious diseases.

Accordingly, the present invention utilizes UV-C lights 34 to reduce the risk of spreading infectious diseases through direct contact with curtains 14, such as those used in healthcare settings. More specifically, the present invention is directed to a curtain sanitizer device 10, 10A, 10B, 100, 100A, 200 and method, such as for use in the healthcare industry, that can sanitize at least a portion of the side surface 12a, 12b of the curtain 14, e.g. a privacy curtain, by directing UV-C radiation 86 thereat to kill or inactivate harmful microorganisms thereon that can cause infectious disease, thereby reducing the risk of spreading infectious disease. The curtain sanitizer device 10, 10A, 10B, 100, 100A, 200 and method can allow the curtain 14 to be cleaned in place, which can be easier to use and less costly and time consuming than other currently available methods and devices.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method and illustrative example shown and described. Accordingly, departures may be made from such details without departing from the spirit or scope of applicant's general inventive concept.

What is claimed is:

1. A curtain sanitizer device comprising:
a base, and spaced apart and opposing first and second elongated walls extending in a vertical direction away from the base, the base including a plurality of legs on a side opposite that of the walls to support the curtain sanitizer device, the first wall including an inner surface that is in opposing relationship to an inner surface of the second wall, with at least one of the inner surfaces configured to accommodate at least one UV-C light, which is capable of killing or inactivating harmful microorganisms on a vertically hung curtain, the space between the inner surface of the walls defining a curtain channel having opposing side openings and an open distal end to allow the vertically hung curtain to laterally pass through the curtain channel with at least a portion of the hung curtain being sanitized by the at least one UV-C light.

2. The device of claim 1 wherein the at least one inner surface includes at least one recessed channel extending along a length of the wall and being configured to accommodate the at least one UV-C light.

3. The device of claim 2 wherein the recessed channel extends approximately centrally along about the length of the wall.

4. The device of claim 1 wherein each inner surface is configured to accommodate at least one UV-C light, which is capable of killing or inactivating harmful microorganisms on the hung curtain.

5. The device of claim 4 wherein each inner surface includes at least one recessed channel extending along a length of the corresponding wall and being configured to accommodate the at least one UV-C light.

6. The device of claim 1 further comprising at least one UV-C light, which is associated with at least one inner surface and capable of killing or inactivating harmful microorganisms on the hung curtain.

7. The device of claim 6 wherein the at least one inner surface includes at least one recessed channel extending along a length of the wall to accommodate the at least one UV-C light.

8. The device of claim 6 wherein the UV-C light defines an elongated tube.

9. The device of claim 6 wherein the UV-C light electrically cooperates with the device to emit UV-C radiation to define a treatment zone in the curtain channel to sanitize at least the portion of the hung curtain as it passes through the curtain channel.

10. The device of claim 1 further comprising at least one UV-C light associated with each inner surface and which is capable of killing or inactivating harmful microorganisms on the hung curtain.

11. The device of claim 1 wherein the inner surface of each wall includes at least one curtain guide that is oriented to mechanically cooperate together to define a gap therebetween that guides the curtain through the curtain channel.

12. The device of claim 11 wherein the curtain guide includes a rotatable wheel.

13. The device of claim 12 wherein the rotatable wheel is motorized.

14. The device of claim 11 wherein the curtain guide includes a belt or track and cooperating rotatable wheels to define a conveyor belt or track.

15. The device of claim 14 wherein the conveyor belt or track is motorized.

16. The device of claim 1 wherein the walls include four pairs of wheels with two pairs being provided on each inner surface, each pair being oriented to mechanically cooperate with another pair on the other inner surface to define gaps therebetween that guide the curtain through the curtain channel.

17. The device of claim 16 wherein each pair of wheels includes a belt or track configured to move thereabout to define a conveyor belt or track, each conveyor belt or track being oriented to mechanically cooperate with another conveyor belt or track on the other inner surface to define gaps therebetween that guide the curtain through the curtain channel.

18. The device of claim 1 wherein each of the walls include first and second spaced apart arms or brush seals that extend generally horizontally along the length of each wall and in a direction away from the inner surface and towards the opposing wall to reduce or eliminate any potential UV-C radiation exposure to users and bystanders when the device is in use.

19. A curtain sanitizer device comprising:
spaced apart and opposing first and second elongated walls extending in a vertical direction and in parallel relation to one another, the first wall including an inner surface that is in opposing relationship to an inner surface of the second wall, with each inner surface configured to accommodate at least one UV-C light, which is capable of killing or inactivating harmful microorganisms on a vertically hung curtain, and a back wall that connects the first and second elongated walls together, the back wall including an outer surface that is configured to be permanently or removably mounted to a wall such that the device defines a wall mounted unit, and the space between the inner surface of the first, second, and back wall defining a curtain channel having only one side opening opposite the back wall and an open distal end to allow the vertically hung curtain to laterally pass through the curtain channel with at least a portion of the hung curtain being sanitized by the at least one UV-C light.

20. The device of claim 19 wherein the inner surface of each of the first and second walls includes at least one recessed channel extending along a length of the corresponding first and second walls and being configured to accommodate the at least one UV-C light.

21. The device of claim 20 wherein the recessed channel is offset from a central position of the inner surface of the corresponding first and second walls in a direction away from the back wall towards the side opening of the curtain channel.

22. The device of claim 19 further comprising at least one UV-C light associated with the inner surface of each of the first and second walls and which is capable of killing or inactivating harmful microorganisms on the hung curtain.

23. The device of claim 22 wherein the UV-C light defines an elongated tube.

24. The device of claim 22 wherein the UV-C light electrically cooperates with the device to emit UV-C radiation to define a treatment zone in the curtain channel to sanitize at least the portion of the hung curtain as it passes through the curtain channel.

25. The device of claim 22 wherein the inner surface of each of the first and second walls includes at least one recessed channel extending along a length of the corresponding first and second walls and being configured to accommodate the at least one UV-C light.

26. The device of claim 25 wherein the recessed channel is offset from a central position of the inner surface of the corresponding first and second walls in a direction away from the back wall towards the side opening of the curtain channel, and further comprising a curtain housing area situated between the inner surface of the back wall and the at least one UV-C light and that accommodates the hung curtain when in a retracted position.

27. The device of claim 19 further including a base and wherein the spaced apart and opposing first and second elongated walls extend in a vertical direction away from the base.

28. The device of claim 19 further comprising a front door that is connected to the first or second wall to allow the front door to be opened and closed, an inner surface of the front door, when the front door is in a closed position, is in opposing relationship to the inner surface of the back wall.

29. The device of claim 19 wherein each of the first and second walls include an arm or brush seal that extends generally horizontally along the length of the wall, in a direction away from the inner surface and towards the opposing wall, and spaced apart from the back wall to reduce or eliminate any potential UV-C radiation exposure to users and bystanders when the device is in use.

30. A method for sanitizing a vertically hung curtain comprising:
passing a vertically hung curtain laterally through a curtain channel of a curtain sanitizer device, the curtain channel including a treatment zone having at least one UV-C light capable of emitting radiation onto at least a portion of one side of the hung curtain; and
subjecting the portion of the one side of the hung curtain to emitted radiation from the UV-C light as the vertically hung curtain laterally passes through the treatment zone, thereby killing or inactivating harmful microorganisms on the portion of the one side of the hung curtain to sanitize the hung curtain.

31. The method of claim 30 further comprising re-orienting the curtain sanitizer device and passing the hung curtain through the treatment zone a second time, and subjecting at least a portion of the other side of the hung curtain to emitted radiation from the UV-C light as the hung curtains passes through the treatment zone, thereby killing or inactivating harmful microorganisms on the portion of the other side of the curtain to sanitize the hung curtain.

32. The method of claim 30 wherein the hung curtain is moved relative to the curtain sanitizer device to pass the hung curtain through the curtain channel of the curtain sanitizer device to sanitize the hung curtain.

33. The method of claim 30 wherein the curtain sanitizer device is moved relative to the curtain to pass the hung curtain through the curtain channel of the curtain sanitizer device to sanitize the hung curtain.

34. The method of claim 30 wherein the hung curtain is a medical curtain.

35. The method of claim 30 wherein at least a portion of opposite sides of the curtain are sanitized simultaneously.

36. The method of claim 30 wherein the hung curtain is manually passed through the curtain channel of the curtain sanitizer device.

37. The method of claim 30 wherein the hung curtain is mechanically passed through the curtain channel of the curtain sanitizer device.

38. The method of claim 37 wherein the hung curtain is mechanically passed through the curtain channel of the curtain sanitizer device via a plurality of rotatable wheels.

39. The method of claim 30 wherein the hung curtain is mechanically passed through the curtain channel of the curtain sanitizer device via a belt or track and cooperating rotatable wheels that define a conveyor belt or track.

40. The method of claim 30 further comprising, prior to passing the hung curtain through the curtain channel of the curtain sanitizer device, positioning and orienting the curtain sanitizer device at a spot along a designated path of the hung curtain to receive the hung curtain.

41. The device of claim 1 wherein each of the legs include a wheel.

42. The device of claim 1 wherein the first and second walls and the base cooperate to define a generally U-shaped configuration.

43. The method of claim 30 wherein the curtain sanitizer device includes a base, and spaced apart and opposing first and second elongated walls extending in a vertical direction away from the base, the base including a plurality of legs on a side opposite that of the walls to support the curtain sanitizer device, the first wall including an inner surface that is in opposing relationship to an inner surface of the second wall, with at least one of the inner surfaces configured to accommodate the at least one UV-C light, which is capable of killing or inactivating harmful microorganisms on the vertically hung curtain, the space between the inner surface of the walls defining the curtain channel having opposing side openings and an open distal end to allow the vertically hung curtain to laterally pass through the curtain channel with at least the portion of the hung curtain being sanitized by the at least one UV-C light.

* * * * *